US 6,674,879 B1

(12) United States Patent
Weisman et al.

(10) Patent No.: US 6,674,879 B1
(45) Date of Patent: Jan. 6, 2004

(54) ECHOCARDIOGRAPHY WORKSTATION

(75) Inventors: Jeffrey Weisman, Dresher, PA (US); Stanley Zietz, Plymouth Meeting, PA (US)

(73) Assignee: Echovision, Inc.

( * ) Notice: Subject to any disclaimer, the term of this patent is extended or adjusted under 35 U.S.C. 154(b) by 0 days.

(21) Appl. No.: 09/647,438

(22) PCT Filed: Mar. 30, 1999

(86) PCT No.: PCT/US99/06999

§ 371 (c)(1),
(2), (4) Date: Nov. 16, 2000

(87) PCT Pub. No.: WO99/49775

PCT Pub. Date: Oct. 7, 1999

Related U.S. Application Data
(60) Provisional application No. 60/079,972, filed on Mar. 30, 1998.

(51) Int. Cl.[7] .................................................. G06K 9/00
(52) U.S. Cl. ......................................... 382/128; 378/94
(58) Field of Search ........................ 382/100, 128–134; 128/653.1, 920; 378/98.2; 600/301, 509; 434/262

(56) References Cited

U.S. PATENT DOCUMENTS

| | | | |
|---|---|---|---|
| 4,730,212 A | 3/1988 | Wojcik et al. ................ 358/83 |
| 4,770,184 A | 9/1988 | Greene, Jr. et al. ..... 128/661.08 |
| 4,771,792 A | 9/1988 | Seale .......................... 128/774 |
| 4,907,973 A | 3/1990 | Hon ............................ 434/262 |
| 5,235,510 A | 8/1993 | Yamada et al. ......... 364/413.02 |
| 5,319,543 A * | 6/1994 | Wilhelm ........................ 705/3 |
| 5,381,791 A | 1/1995 | Qian ........................... 128/659 |
| 5,416,602 A | 5/1995 | Inga et al. .................. 358/403 |
| 5,619,995 A * | 4/1997 | Lobodzinski ............ 128/653.1 |
| 5,644,612 A | 7/1997 | Moorman et al. .......... 378/98.2 |
| 5,687,737 A * | 11/1997 | Branham et al. ............ 600/509 |
| 5,769,641 A * | 6/1998 | Lampotang et al. ......... 434/262 |
| 5,878,746 A * | 3/1999 | Lemelson et al. ........... 128/920 |
| 5,961,448 A * | 10/1999 | Swenson et al. ............ 600/301 |
| 6,113,540 A * | 9/2000 | Iliff ............................ 128/920 |
| 6,115,486 A * | 9/2000 | Cantoni ...................... 382/128 |
| 6,205,199 B1 * | 3/2001 | Polichar et al. ............ 378/98.2 |
| 6,267,599 B1 * | 7/2001 | Bailey ......................... 345/156 |

* cited by examiner

Primary Examiner—Jayanti K. Patel
(74) Attorney, Agent, or Firm—Woodcock Washburn LLP

(57) ABSTRACT

A digital image processing system for enhancing the image quality and diagnostic capabilities of conventional medical diagnostic ultrasound imaging systems and, more particularly, to an echocardiography workstation (10) which provides speckle reduction (200), edge detection, color quantitation (306), automatic diagnostic features. a built-in Help system for echocardiography, automatic quantitative analysis of left ventricular function, tomographic perfusion display (36), 3-D analysis, and report generation for improved analysis of echocardiograms.

46 Claims, 13 Drawing Sheets

Left Ventricular Boundary Location

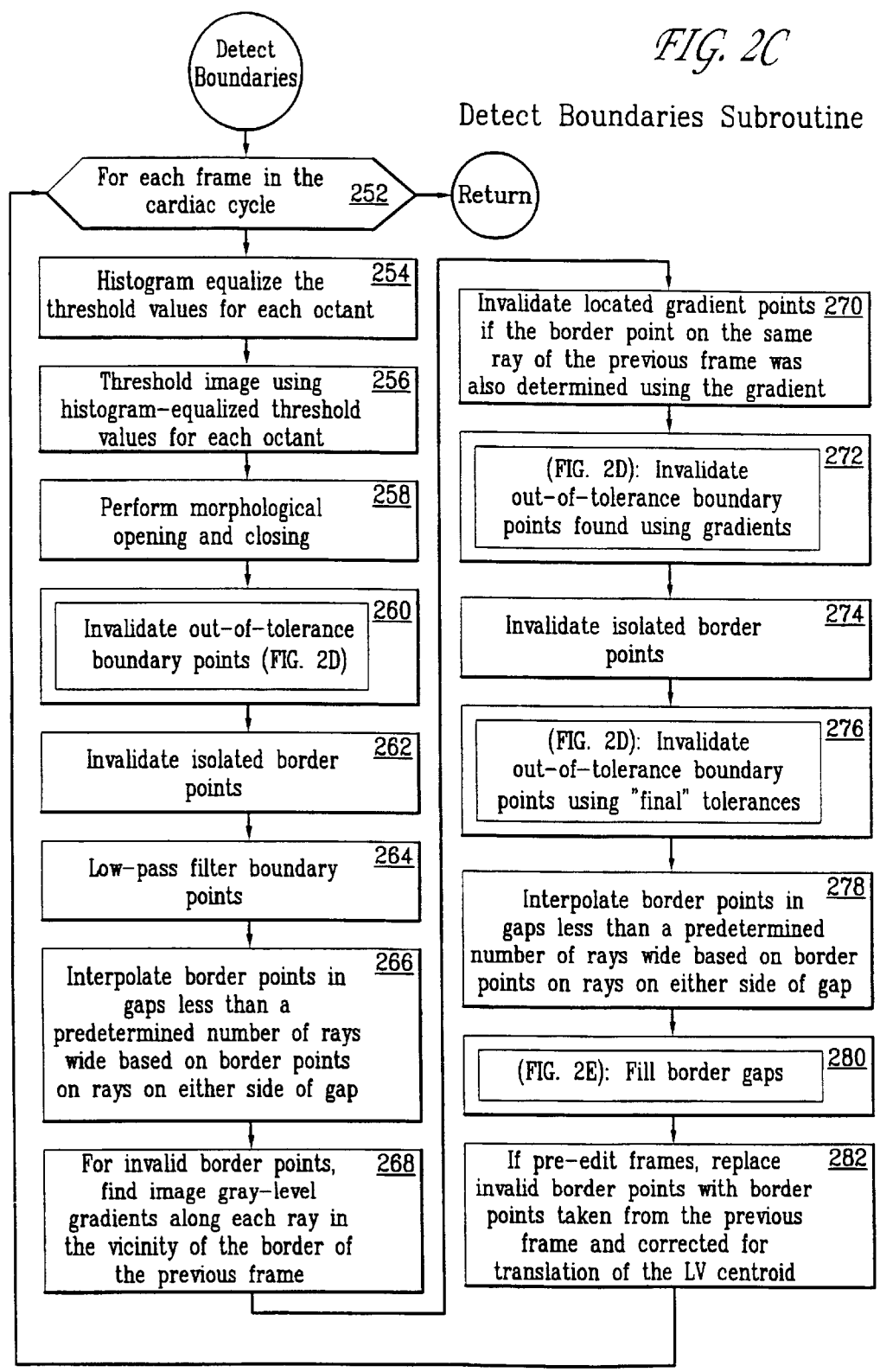

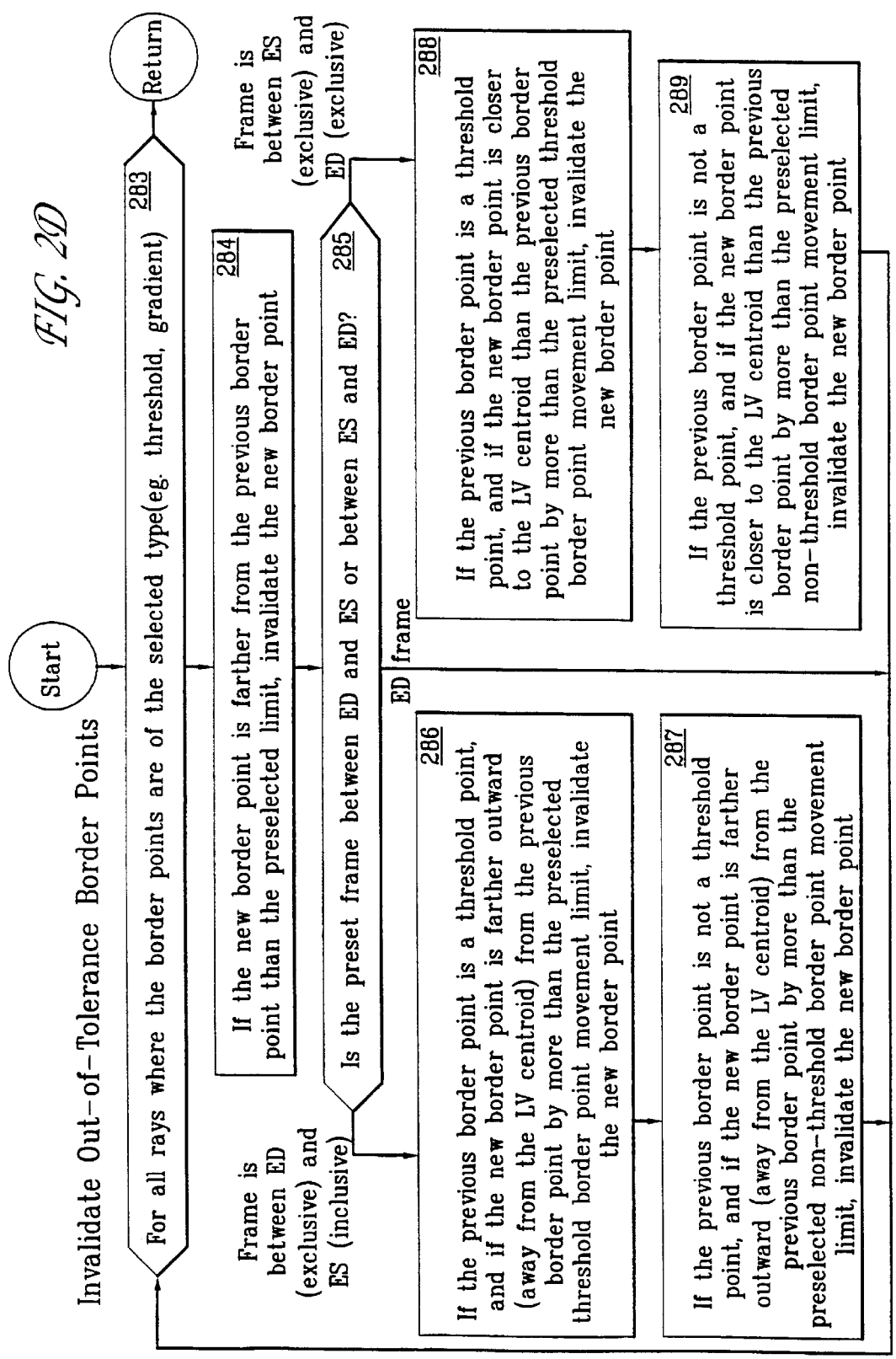

Color Quantitation

FIG. 10

Echocardiography Report

Name: elise b weisman  
Weight:  
BSA:  
D.O.B:

Study Date: 3/14/98  
Referring Physician: weisman  
Tape Number:  
Study Number: 1  
Sonographer:

Reason for Study / Diagnosis: Palpitation

Measurements

| AO Root | Cusp Sep | LA | LVOT Diam | IVS(d) | LVPWT | EF | RA Dimension |
|---|---|---|---|---|---|---|---|
| | 1.10 | 5.70 | | 1.70 | 1.10 | | |

Doppler

| | Regurgitation | Peak Gradient | Mean Gradient | Aortic Valve Area |
|---|---|---|---|---|
| Aortic: | Severe | 70.00 | 40.00 | 1.60 |
| Mitral: | Moderate | 12.00 | 6.00 | 1.80 |
| Tricuspid: | Moderate | | | |
| Pulmonic: | Mild to Moderate | 70.00 | 70.00 | |

Aorta: Unable to Assess  
Aortic Valve: Morphology: Unable to Assess | Thickened Mild to Moderate  
Motion: Unable to Assess | Reduced Cusp Separation Left Atrium: Dilated Moderate  
Left Ventricle: Aorta: Dilated  
Aorta: Unable to Assess | Segmental

Wall Thickness  
Mitral Valve: Morphology: Thickened Anterior – Mild  
Motion: Normal

ECHOCARDIOGRAPHY WORKSTATION

This application claims the benefit of provisional application Ser. No. 60/079,972 filed Mar. 30, 1998.

Field of the Invention

This invention relates to a digital image processing system for enhancing the image quality and diagnostic capabilities of conventional medical diagnostic ultrasound imaging systems and, more particularly, to an echocardiography workstation which provides speckle reduction, edge detection, color quantitation, automatic diagnostic features, a built-in Help system for echocardiography, automatic quantitative analysis of left ventricular function, tomographic perfusion display, 3-D analysis, and report generation for improved analysis of echocardiograms.

BACKGROUND OF THE INVENTION

Diagnostic ultrasound applies high frequency pulsed and continuous sound waves to the body and uses computer-assisted processing of the reflected sound waves to develop images of internal organs and the vascular system. The waves are generated and recorded by transducers or probes that are either passed over or inserted into the body. The resulting images can be viewed immediately on a video display or can be recorded for later evaluation by the physician in continuous or single image formats.

Diagnostic ultrasound imaging is now the preferred imaging modality in radiology, cardiology, and obstetrics and gynecology. Cardiologists and other medical practitioners use cardiac ultrasound imaging, or echocardiography, to evaluate the condition of the heart. Echocardiography is quick, relatively inexpensive, convenient, safe, and non-invasive, and can be performed in real-time in private offices as well as hospitals. The primary drawback of echocardiography has been the difficulty of acquiring good quality images in patients with poor acoustic windows. These patients are estimated to comprise 10–30 percent of the patient population. Moreover, speckle noise and poor resolution can compromise the clinical utility of images of any patient produced by even the most sophisticated ultrasound scanners. With echocardiography, the difficulty of acquiring acceptable images is further compounded by the fact that the region of interest, the heart, has complex motion patterns.

As a result of poor image quality, up to 10 percent of all rest echo studies and up to 30 percent of all stress echo studies of patients are non-diagnostic. The most important factor is the presence of speckle noise, produced by the random pattern of overlapping echos that results from the scattering of the reflected sound waves. This pattern degrades contrast resolution and reduces the ability of an observer to discriminate tissue boundaries and subtle image variations. Techniques for reducing such speckle noise while preserving and enhancing the integrity of the myocardial borders and other cardiac structures remain highly desirable.

Conventional echocardiographic assessment of heart function requires the delineation of the endocardial borders throughout the cardiac cycle. In the images produced by conventional scanners, these borders are often obscured by speckle, masking, blurring, low contrast and interpolation. In addition, discontinuities frequently appear in the echocardiographic image due to poor lateral resolution, which is inherent to ultrasound imaging because portions of the cardiac border are always located parallel to the illuminating sonic beam. Such border definition difficulties are accentuated when performing stress echo studies, making it very difficult to track the endocardial contours. A robust edge detection/contour tracking algorithm is desired that can be used effectively in both rest and stress echocardiography.

In addition, while there are accepted global and regional quantitative measures of cardiac function, there are currently no effective tools that provide automatic quantitation of segmental cardiac function by echocardiography; rather, there are only qualitative assessment or manual quantitative methods which are time-consuming and subject to observer error. Moreover, previous attempts at displaying cardiac wall motion based on boundary detection systems have improperly delineated the endocardial border and blended other signals between the endocardium and other heart structures, such as papillary muscles, chordae, or mitral valve tissue. It remains desirable to provide reproducible automatic quantitation of global indices and regional wall motion and to display the results in a readily understandable format, such as a color-coded format, whereby the effect of therapy and the evolution of disease may be more readily understood.

Also, at present, there are no systems known to the inventors which provide the physician with automatic interpretation assistance for specific echocardiograms and offer the physician various diagnostic possibilities that are consistent with the available data. Conventional echocardiography review and reporting systems are off-line computer systems which are equipped with graphical tools and data entry screens that facilitate on-screen measurement of digitized images and the generation and archiving of reports. Such systems are not configured to capture video images, to perform image enhancement, edge detection, and 3-D image analysis, or to perform stress echo studies. Such systems are also very expensive. A cost-effective off-line and/or on-line analysis and report generation system remains desirable.

Accordingly, it is desired to provide a user-friendly echocardiography workstation that improves image quality, provides automatic edge detection, quantitates endocardial wall movement, corrects for cardiac translation, calculates 3-D left ventricle volume, and assists the physician with the interpretation of echocardiograms. The present invention has been designed to meet these needs in the art.

SUMMARY OF THE INVENTION

The present invention addresses the above-mentioned needs in the art by providing an echocardiography workstation that combines video capture and quad screen display for rest and stress echocardiography, speckle reduction, edge detection, and cardiac contour tracking, automatic diagnostic interpretation assistance, a built-in reference source (HELP) to assist the physician and technologist with evaluating echocardiograms, color quantitation, report generation, and automatic wall motion analysis in a single system. The system also includes an optional 3-D feature which utilizes a spatial locating device to obtain tomographic slices along a reference plane which are used for 3-D reconstruction. The workstation of the invention thus complements conventional cardiac ultrasound scanners to enhance the image quality of echocardiograms and to automate functions that have previously been performed manually, thereby saving physician time and reducing costs, while also improving the capabilities of the cardiac scanner.

The workstation of the invention can be used to digitize the video output of cardiac ultrasound scanners. The user can then apply noise reduction algorithms that not only reduce excessive noise but also enhance the definition of cardiac structures. The enhanced images are further processed by boundary detection algorithms to automatically identify the endocardial border and to track its movement through the cardiac cycle. The resulting delineation of the cardiac wall motion allows the physician to more quickly and accurately evaluate heart function. The system corrects for cardiac translation and the extent of cardiac function (motion) is reproducibly automatically quantitated and displayed in a color-coded format which simplifies the physician's review process. Also, during the physician's review process, expert system software assists the physician in the interpretation process by listing the various diagnostic possibilities that are consistent with the available data. A Help system assists the physician with the interpretation of the data by providing descriptions of abnormalities with lists of their known causes.

The workstation of the invention may also be used with spatial locators that register the position and orientation of two-dimensional ultrasound images in a three-dimensional spatial coordinate system. This feature enables the system to perform more accurate calculations of cardiac function. The workstation also provides tomographic analysis software to permit the display of myocardial perfusion data for use in conjunction with ultrasound contrast agents. The invention also includes an R-wave synchronization feature to synchronize images of varying frame lengths and heart rates.

Preferably, the physician interacts with the workstation through a graphical user interface or by voice commands to view images, select alternative processing options, consult reference sources, generate reports from pull-down menus, and store, retrieve, and transmit digitized images and reports.

BRIEF DESCRIPTION OF THE DRAWINGS

The foregoing and other novel features and advantages of the invention will become more apparent and more readily appreciated by those skilled in the art after consideration of the following description in conjunction with the associated drawings, of which:

FIGS. 2a–2e together illustrate a currently preferred embodiment of an algorithm for determining the left ventricular boundary location in a received echocardiogram for contour tracking and quantitative analysis of left ventricular function.

FIG. 10 illustrates a sample echocardiography report generated by the report generator of the invention.

DETAILED DESCRIPTION OF THE PRESENTLY PREFERRED EMBODIMENTS

Figure 1:
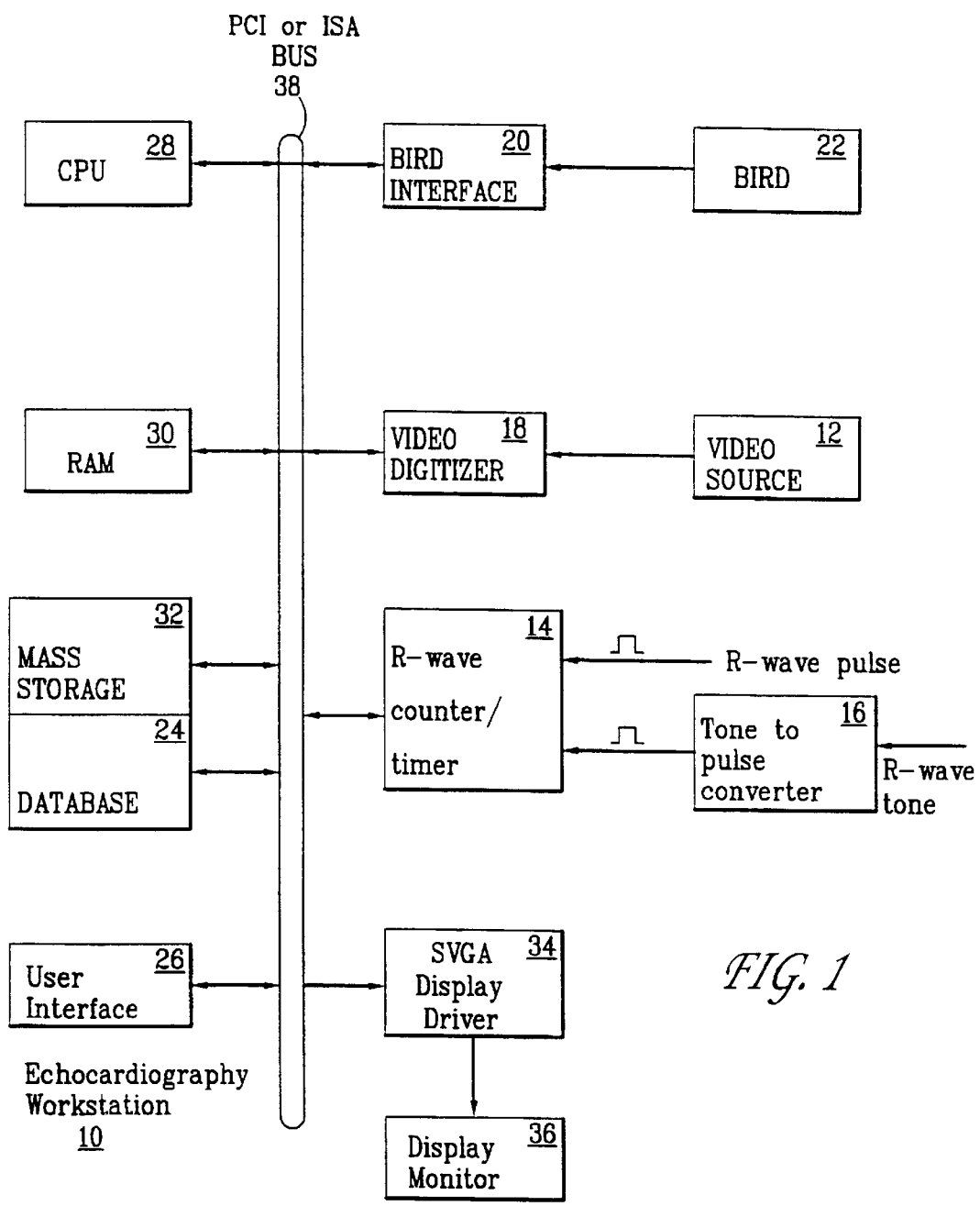
FIG. 1 illustrates a generalized block diagram of an echocardiography system in accordance with a currently preferred embodiment of the invention.

A preferred embodiment of the invention will now be described in detail with reference to FIGS. 1–10. Those skilled in the art will appreciate that the description given herein with respect to those figures is for exemplary purposes only and is not intended in any way to limit the scope of the invention. For example, those skilled in the art will appreciate that while the preferred embodiment of the invention relates to the ultrasonic imaging and analysis of the heart that the invention may be readily adapted for the imaging and analysis of other internal organs and structures. Furthermore, the invention described herein may be applied to other imaging modalities including MRI, CAT scan, angiography, and others in which speckle noise reduction and image edge detection may be desirable. All questions regarding the scope of the invention may be resolved by referring to the appended claims.

As will be explained in more detail below, the echocardiography workstation of the invention provides for image enhancement, edge detection, quantitation, and assistance in the interpretation of echocardiograms and the generation of reports as well as a Help system for echocardiography. The echocardiography workstation is an integrated hardware/software system which is compatible with conventional cardiac ultrasound machines and blends digital image processing functions with administrative capabilities in an interactive system that dramatically improves the productivity of mainstream cardiologists.

The echocardiography workstation of the invention can be used to digitize the video output of the cardiac ultrasound system. It then applies the noise reduction algorithms, which not only reduce excessive noise, but also enhance the definition of cardiac structures. The enhanced images may, if selected by the user, undergo further processing by boundary detection algorithms to automatically identify the endocardial border and to track its movement through the cardiac cycle. Indices of cardiac function are automatically calculated by quantitation software, and the results are displayed in color-coded format for immediate review by the physician or technician. An integrated expert system alerts the physician to various diagnostic possibilities that are consistent with the available data, including patient history and data from earlier studies that are stored in the workstation database.

The physician interacts with the echocardiography workstation through a graphical user interface or by voice commands to view images, to select alternative processing options, to consult reference sources, to generate reports from pull-down menus, and to store, retrieve and transmit digitized images and reports. Reports that conventionally may require hours or even days to produce and transmit to referring physicians can be completed and communicated electronically in a matter of seconds.

The methods and apparatus of the present invention, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the invention. The methods and apparatus of the present invention may also be embodied in the form of program code that is transmitted over some transmission medium, such as over electrical wiring or cabling, through fiber optics, or via any other form of transmission, wherein, when the program code is received and loaded into and executed by a machine, such as a computer, the machine becomes an apparatus for practicing the invention. When implemented on a general-purpose processor, the program code combines with the processor to provide a unique apparatus that operates analogously to specific logic circuits.

FIG. 1 illustrates a generalized block diagram of an echocardiography workstation 10 in accordance with a currently preferred embodiment of the invention. As shown in FIG. 1, the workstation 10 receives a video signal from an echocardiographic machine including video source 12 and an R-wave counter/timer 14 which receives an R-wave pulse directly or from a tone to pulse converter 16. As shown, a video digitizer 18 digitizes the received video signal for further processing. In the preferred embodiment, the workstation 10 also receives spatial information via a spatial locator interface 20 from a spatial locator device 22, such as a BIRD™ electromagnetic tracking system, which measures the real-time position and orientation (six degrees of freedom) of one or more miniaturized sensors for correlating the ultrasound image location with the patient's body. The workstation 10 also receives diagnostic information from an expert system database 24 for use in automatically evaluating the received echocardiogram. As will be explained in more detail below, the user interface 26 allows the user to select the desired processing and display features. These inputs are processed by conventional computer elements including processor 28, RAM 30, mass storage 32 (which may or may not include the expert system database 24), display driver 34, and display monitor 36. Generally, each of these elements is connected by a PCI or ISA data bus 38 so as to communicate data in a conventional fashion. Processor 28 functions by processing the software for implementing the speckle reduction, edge detection, color quantitation, report generation, and database management algorithms, and the like, of the type described herein.

In a preferred embodiment, the digitized video images from the video digitizer 18 are stored in mass storage 32 and/or RAM 30 as a frame consisting of four subframes (Quad frame representation). In other words, the memory is divided into N logical image frames of the height (H) and width (W) of the image to be displayed, and each logical frame is divided into four logical quadrants of size H/2 by W/2. This approach allows four concurrent viewing windows to be synchronized for display so that different views of a region or live and digitized reference views may be viewed concurrently. Preferably, the first frame of a stored image sequence is also displayed in the main viewing area of the display 36 as a miniaturized thumbnail icon for easy retrieval of the corresponding image sequence.

The processes of image capture, synchronization of different images using the R-wave, and generating the aforementioned quad screen image display will now be described.

Image Capture:

To capture echocardiogram images, the workstation 10 waits for next R-wave pulse from R-wave counter/timer 14. Upon receipt of the R-wave pulse, the received video signals from video source 12 are digitized by video digitizer 18 at 30 frames per second. As noted above, each frame of video is stored into contiguous logical image frames or into a pre-selected quadrant of contiguous logical image frames of the host memory 30 or 32, where different views may be shown in each quadrant. The R-wave counter/timer 14 is interrogated when each frame is captured to determine if an R-wave pulse (event) occurred during the time of the frame capture. If so, the frame identifier is stored in a list of frame identifiers containing frame identifiers of all frames with an associated R-wave pulse (event). This process continues until either (a) a pre-selected number of R-wave pulses (cardiac cycles) have been captured, or (b) the host memory 30 or 32 is filled. Once image capture is complete, the image quadrants are synchronized (R-wave synchronization) as described below.

During the performance of the ultrasound investigation, the technician can select key image sequences to digitize to RAM 30 and to store to the hard drive or mass storage 32. When performing a rest echo, a full screen (640×480) or quad screen is digitized. The images are digitized using R-wave triggering device 14 that senses the R-wave voltage or the audio beep. A menu allows the user to choose to digitize systole, diastole or both. The user may chose the number of R-wave cycles to capture. The acquired images can then be processed as described below.

R-wave Synchronization:

Since up to four image sequences are displayed concurrently in accordance with the invention, and since each cardiac cycle may contain a different number of frames than other cardiac cycles, and since the displayed cardiac cycles of each of the (up to) four simultaneously displayed image sequences must contain the same number of frames, frames are added to the image sequences that contain fewer frames per cardiac cycle than the displayed sequence with the most frames per cardiac cycle as follows.

Target frame counts are computed for systolic and diastolic portions of the cardiac cycle, where the target systolic frames are $\sqrt{3.6N}$ and the target diastolic frames are N minus the target systolic frames, where N is the number of frames in the selected cardiac cycle of the sequence with the maximum number of frames in the cycle. Then, for each cardiac cycle of each image sequence, the number of systolic frames to add and the number of diastolic frames to add are computed as follows.

The number of systolic frames to add is the target systolic frame minus $\sqrt{3.6N}$, and the number of diastolic frames is the target diastolic frame minus $(N-\sqrt{3.6N})$, where N is the number of frames in the cardiac cycle. The systolic frames are then repeated from frame $\sqrt{3.6N}$ to frame ($\sqrt{3.6N}$ minus the add systolic frame number), while the diastolic frames are repeated for all frames in the range $\sqrt{3.6N}+1$ to N by int(add diastolic frames/$\sqrt{3.6N}$) times. All frames in the range $M=\sqrt{3.6N}+[N-\sqrt{3.6N}-\text{MOD}(\text{add diastolic frames})*\sqrt{3.6N})]/2$ to $M+\text{MOD}(\text{add diastolic frames}, \sqrt{3.6N})$ are repeated one time each. If any of the sequences contains fewer cardiac cycles then the others, the last cardiac cycle is repeated the required number of times.

Image Display:

At a rate of 30 frames per second, the sequential logical image frames (entire frames, not quads) are transferred from the host memory 30 or 32 to the display driver 34 for display on display monitor 36. The display starts on the selected frame and resets to the first selected frame after the last selected frame has been displayed, where the selected frames are usually those frames contained in one or more cardiac cycles. A cardiac cycle begins with the frame during which an R-wave pulse occurred to the frame just prior to the frame during which the next R-wave pulse occurred. Slow motion is implemented by displaying each frame N times before moving to the next frame, and fast motion is implemented by skipping frames in the sequence during display.

Spatial Location

Preferably, the technician can utilize the spatial locator 22 to allow the capture of specific orthogonal slices and the calculation of 3-D ventricular volumes for the rendering of a 3-D model of the beating heart. For this purpose, a spatial locator 22 such as the Bird™ from Ascension Technologies is attached to an ultrasound transducer. This device allows tracking of the spatial location of the transducer using 6 degrees of freedom information, whereby the images are acquired at "IN" degree intervals with the 6 degrees of freedom coordinates stored with each image. Preferably, a reference image sequence so acquired is digitized by video digitizer 18 and stored in host memory 30 or 32. For 3-D imaging, all images are displayed on a 3-D background or 3-D background with a translucent 3-D model of the heart overlaid onto the 2-D slices to indicate the slice position as it relates to the 3-D model. On the other hand, the reference image sequence may be displayed in one quadrant of the display 36, while the live video is displayed in another quadrant of the display 36. Then, as the technician moves the transducer, the coordinates from the spatial locator 22 cause the cursor on the reference image to move, showing the location of the orthogonal slice in the live image in relation to the reference image or in relation to the 3-D model.

Once the image is digitized, synchronized, and displayed, the operator may elect to perform various operations on the displayed images to extract relevant information both for visual enhancement and quantitative analysis. This process will now be described with respect to FIGS. 2–4.

Figure 2A:
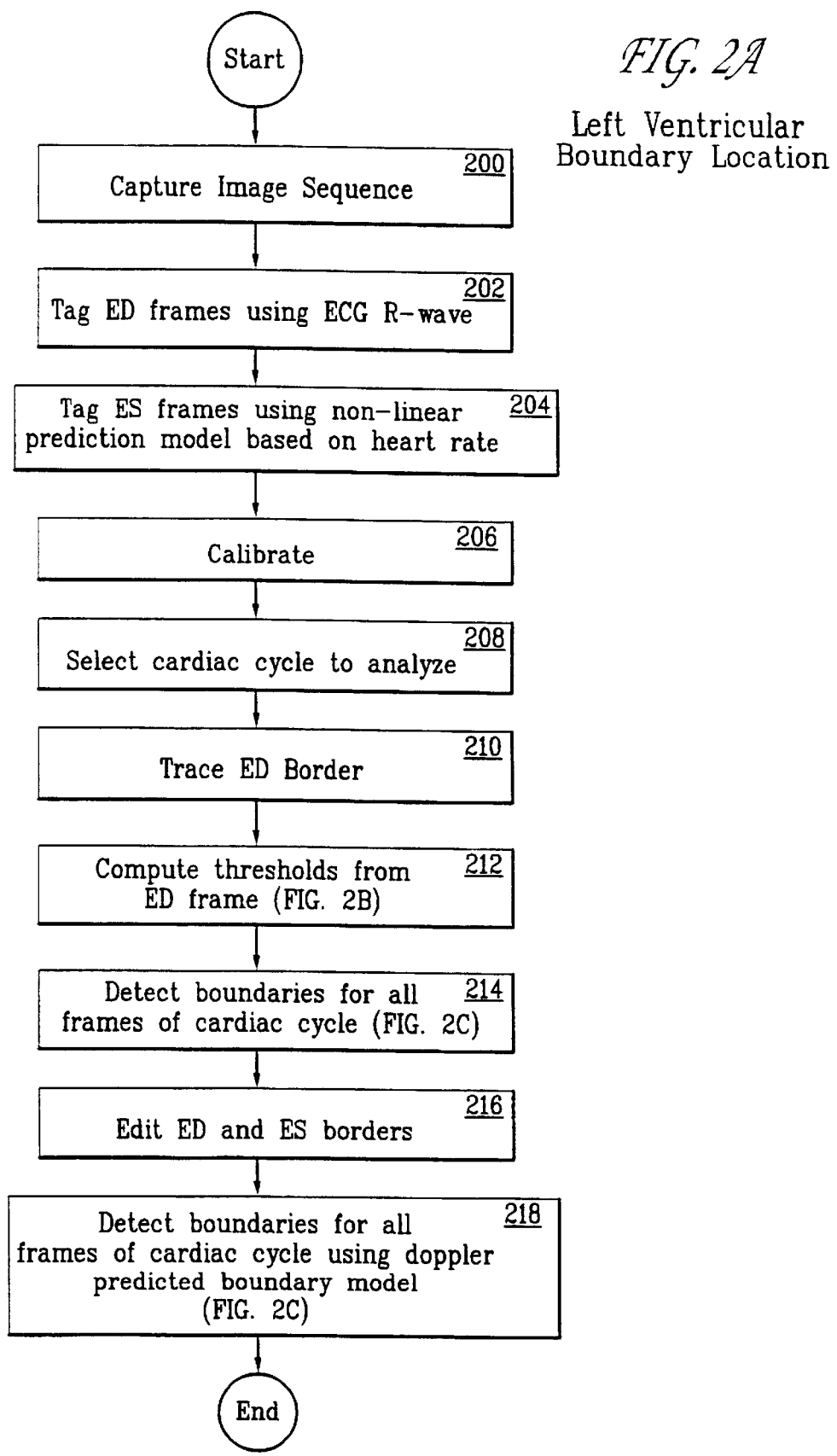

As illustrated in FIG. 2a, the first step in the processing of the displayed images is to capture the image sequence as described above at step 200. In a preferred embodiment of the invention, the image capture step further includes the step of utilizing a speckle reduction algorithm to acquire a speckle reduced image by performing speckle reduction on the displayed images to increase the signal-to-noise ratio of the video and to enhance features of the echocardiogram image. In the preferred embodiment of the invention, the speckle reducing two-dimensional filtering is a three step process.

First, a non-linear gray scale transformation is performed on each image in a sequence. In particular, each of the original 256 gray scale image levels is mapped non-linearly to another gray scale image level which is selected to enhance image contrast of the individual images. Typically, each pixel of each image in the sequence is remapped according to a pre-stored look-up table taken from a class of look-up tables that has the shape illustrated generally in FIG. 3.

Second, recursive averaging is applied to the image sequence. In particular, each pixel in two or three consecutive frames is combined with the pixel in the same position in the previous and/or subsequent (in time) frame as:

pixel(present frame)=persistence*pixel(present frame)+(1−persistence)*pixel(previous frame), where "persistence" is selected by the user. Typical values for persistence are 0.3, 0.4, 0.5, 0.6 and 0.7.

Finally, a two-dimensional non-linear gray level morphology operation is performed on each pixel of an individual image. This operation is described as follows:

| 4 | | 1 | | 3 |
|---|---|---|---|---|
| | 4 | | 1 | |
| | | | | 3 |

-continued

| 2 | | X | 2 | 2 |
|---|---|---|---|---|
| | 3 | 1 | 4 | |
| 3 | | 1 | | 4 |

A square neighborhood of each pixel of the image is chosen. The above diagram represents a 5 by 5 neighborhood of the central pixel marked x. The user is given the option of using a 3 by 3, 5 by 5 or 7 by 7 neighborhood. On this neighborhood, four directions containing the pixel x are chosen. In this diagram, the four sets of points are labeled 1,1,x,1,1; 2,2,x,2,2; 3,3,x,3,3; 4,4,x,4,4. Each of these sets contains the central pixel x and four other points. For each of these sets, the maximum number of the set is found as well as the minimum of these four maximums. The minimum number of each set is also found as well as the maximum of these four minimums. Finally, the pixel x is replaced with the average of these two numbers (the minimum of the maximums and the maximum of the minimums).

The above operation is performed for all the pixels in the image, with special processing for edge effects. The process is then iterated a given number of times which is controlled by the user. Presently, the user may select 1, 2, 3, 4, or 5 iterations.

Once the above filtering is applied to the video sequences and the image is captured at step 200, it is determined by the user whether or not to proceed with further processing. If so, the user determines whether the displayed images have adequate quality. If so, the edge detection of FIGS. 2a–2e is performed; otherwise, the video signal may be processed to improve image quality prior to the edge detection processing. The frame corresponding to end-diastole and the frame corresponding to end-systole may be automatically brought up, where the frame corresponding to end-systole is found as an offset from the diastolic frame as determined by the equation: systolic frame offset=sqrt(3.6*number of frames in cardiac cycle) as set forth above.

As will be explained in detail below, using the R-wave detector 14, the end-diastolic frame is automatically displayed so that the user may trace the diastolic border on this frame or select the center of the blood pool of the end-diastolic frame so that this frame is automatically traced and so that the endocardial wall on the current and subsequent frames may be automatically detected by performing the edge detection process of FIGS. 2a–2e.

FIGS. 2a–2e together illustrate a currently preferred embodiment of an algorithm for edge detection in accordance with the invention. By way of example, the edge detection algorithm is described in connection with the determination of the left ventricular boundary location in the received image for contour tracking and quantitative analysis of the left ventricular function.

Once the digitized image sequence from video digitizer 18 is captured and the above-mentioned speckle reduction performed at step 200, the end diastolic (ED) frames are tagged using the ECG R-wave at step 202. The end systolic (ES) frames are also tagged at step 204 preferably using a non-linear prediction model based on the patient's heart rate. The system is then calibrated at step 206, as necessary.

At step 208, the reviewer selects the cardiac cycle to be analyzed and traces the ED border at step 210 or selects the center of the blood pool of the ED frame and the ED border is automatically traced. Thresholds are then computed from the ED frame at step 212 preferably using the algorithm described below with respect to FIG. 2b. Pre-edit boundaries for all frames of the cardiac cycle are then detected at step 214 preferably using the algorithm described below with respect to FIGS. 2c–2e. The ED and ES borders may then be manually edited at step 216 before repeating the boundary detection algorithm of FIG. 2c for detection of the post-edit boundaries for all frames of the cardiac cycle at step 218. As set forth in FIG. 2e, the edited points may incorporate the Doppler predicted boundary points to fill in gaps in the edge data. Performing this process for each frame allows the physician or technician to track the heart's contours during the diagnostic evaluation.

Figure 2B:
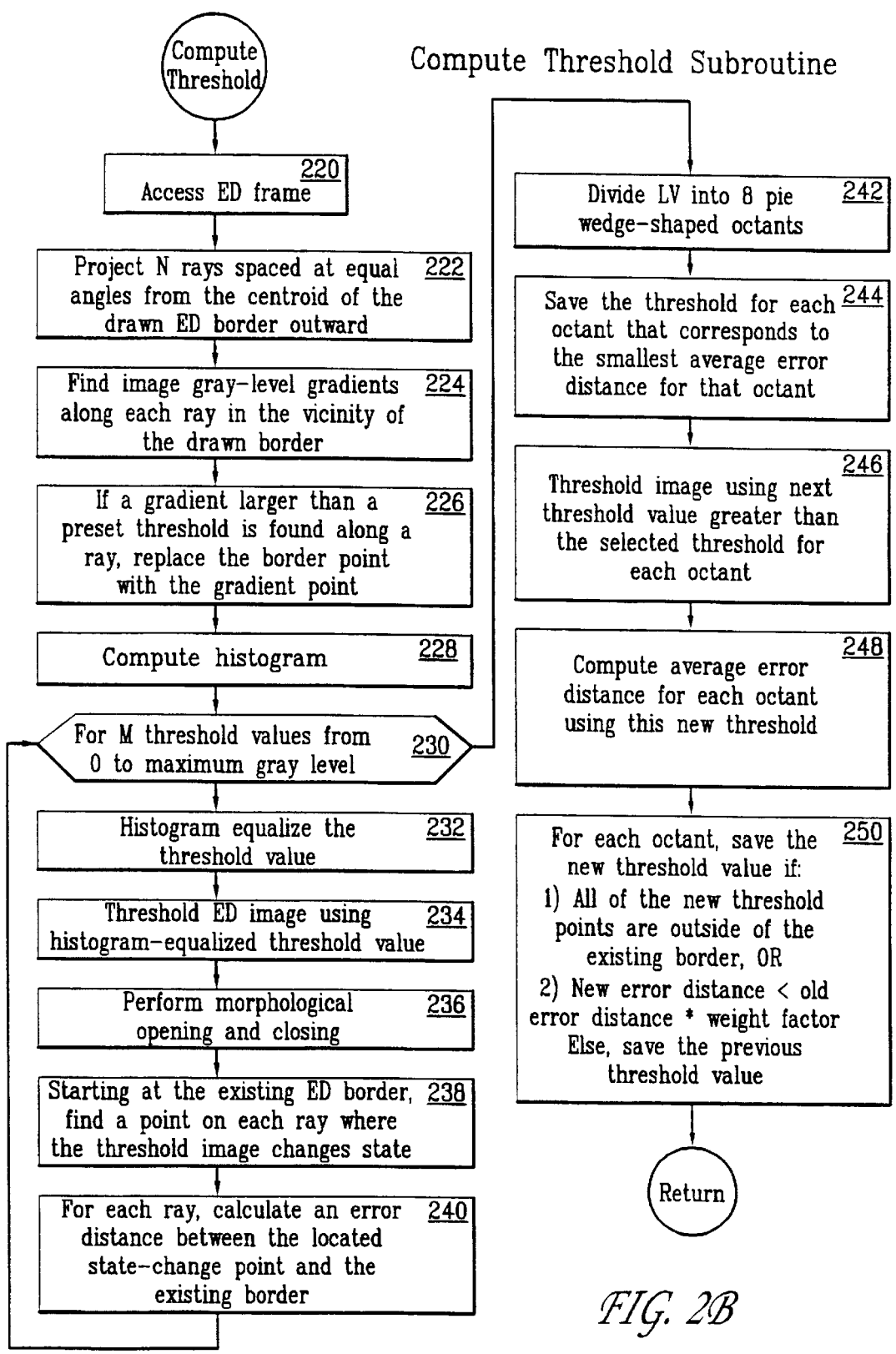

FIG. 2b illustrates in more detail a preferred embodiment of the threshold computation algorithm implemented in step 212. As illustrated, the ED frame is accessed at step 220, and N rays are projected which are spaced at equal angles from the centroid of the drawn ED border (determined at step 210) outward at step 222. At step 224, the image gray-level gradients along each ray in the vicinity of the drawn border are found, and, if a gradient larger than a preset threshold is found along a ray, the border point is replaced with the gradient point at step 226. A histogram is then computed at step 228.

Next, for each of M threshold values from 0 to a maximum gray level (step 230), the threshold value is histogram equalized (step 232), the ED image is thresholded using the histogram equalized threshold value (step 234), and morphological opening and closing is performed (step 236). Also, starting at the existing ED border, a point is found on each ray where the thresholded image changes state (step 238). Then, for each ray, an error distance between the located state-change point found in step 238 and the existing border is calculated at step 240. Once this process has been performed for each of the M threshold values, processing proceeds to step 242.

At step 242, the left ventricle is divided into 8 pie wedge-shaped octants. The threshold for each octant that corresponds to the smallest average error distance for that octant is then saved at step 244. The image is then thresholded at step 246 using the previously selected threshold value or next threshold value greater than the previously selected threshold for each octant. The average error distance for each octant is then computed at step 248 using the new threshold. Finally, at step 250, for each octant, the new threshold value is saved if all of the new threshold points are outside of the existing border or the new error distance is less than the older error distance multiplied by some weighting factor. Otherwise, the previous threshold value is saved.

FIG. 2c illustrates in more detail a preferred embodiment of the boundary detection algorithm implemented in steps 214 and 218. As illustrated in FIG. 2a, the process repeats steps 252–282 twice for each frame in the cardiac cycle, once prior to editing (step 214) and once after editing (step 218). In each loop, the threshold values for each octant are histogram equalized at step 254, and the image is thresholded at step 256 using the histogram equalized threshold values for each octant. Morphological opening and closing is performed at step 258, and out-of-tolerance boundary points are invalidated at step 260, preferably using the algorithm of FIG. 2d. Isolated border points are invalidated at step 262, and the boundary points are then low pass filtered at step 264. The filtered border points are then interpolated at step 266 in gaps less than a predetermined number of rays wide based on the border points on rays on either side of the gap.

Figure 2E:
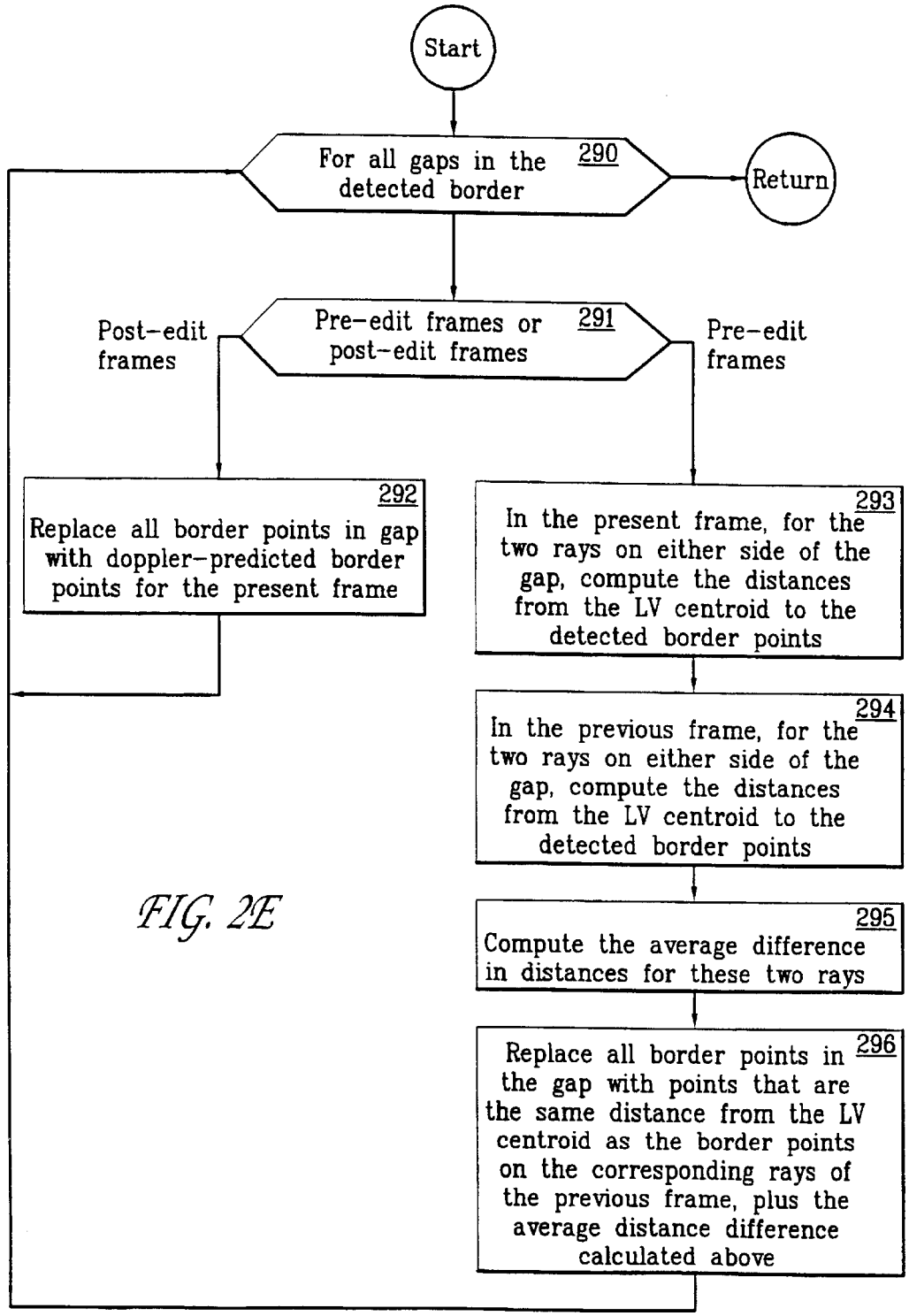
Figure 3:
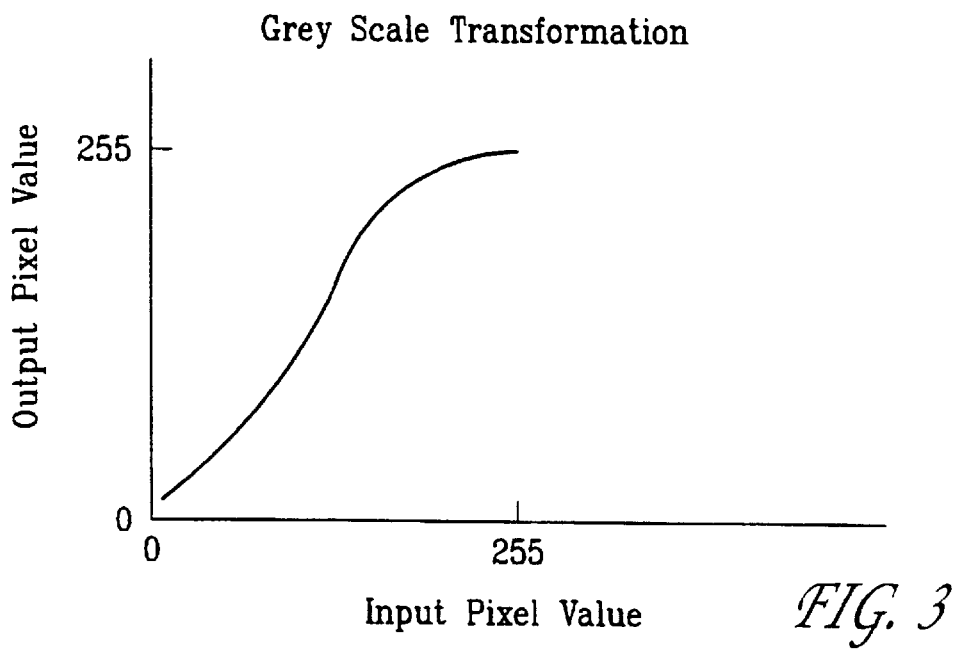
FIG. 3 illustrates a currently preferred embodiment of a non-linear gray scale transformation curve implemented in the speckle reduction technique of the invention.
Figure 4:
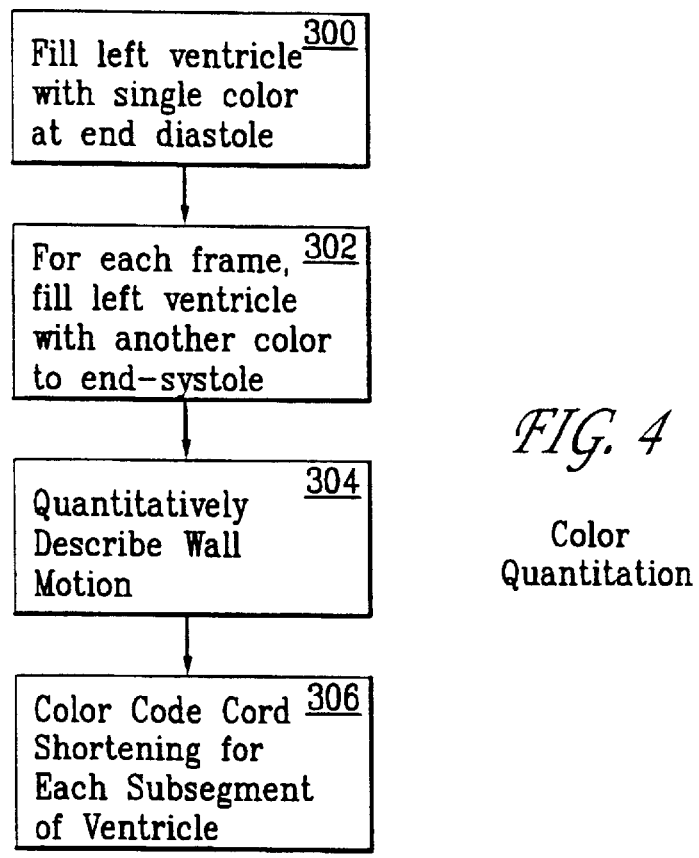
FIG. 4 illustrates a currently preferred embodiment of an algorithm for the color quantitation of endocardial wall motion in accordance with the invention.

At step 268, the image gray-level gradients along each ray in the vicinity of the border of the previous frame are found for invalid border points, and the located gradient points are invalidated at step 270 if the border point on the same ray of the previous frame was also determined using the gradient. Out-of-tolerance boundary points found using the gradients are then invalidated at step 272, preferably using the algorithm of FIG. 2d. Once again, isolated border points are invalidated at step 274, and out-of-tolerance boundary points using "final" tolerances are invalidated at step 276. Border points are then interpolated at step 278 in gaps less than a predetermined number of rays wide based on the border points on rays on either side of the gap. At step 280, pre-edit border gaps are filled from the border of the previous frame, preferably using the algorithm of FIG. 2e, while post-edit border gaps may be filled with Doppler predicted border points as also illustrated in FIG. 2e. Finally, in the case of pre-edit frames, invalid border points are replaced at step 282 with border points taken from the previous frame and corrected for translation of the left ventricle (LV) centroid from the previous frame to the current frame. The process then repeats for the next frame in the cardiac cycle.

In step 282, the translation of the LV centroid is corrected in a preferred embodiment as follows. After outlining the contour on two adjacent frames, the contour from the earlier frame is divided into a number of points equally spaced with respect to arc length. The contour of the later frame is then divided into a number of points equally spaced again with respect to its arc length. Preferably, the number of points of the second contour is triple the number of points of the first contour. For each point in the original contour, the point on the second contour nearest to that point is then found, and the area of the quadrilateral defined by two adjacent points on one contour and the points nearest to them on the next contour determines the distance that part of the heart wall is determined to move during the time interval. This procedure is then iterated on subsequent contours. A variant of this procedure may be used with certain contours whereby the points on that contour are not re-normalized with respect to arc length; rather, the nearest points on that contour are used as the initial division when finding the points on the next contour (un-renormalized condition).

FIG. 2d illustrates in more detail a preferred embodiment of the algorithm for invalidating out-of-tolerance border points implemented in steps 260, 272 and 276. As illustrated, the process starts at step 283 and repeats for all rays where the border points are of the selected type (e.g., threshold or gradient). At step 284, it is determined if the new border point is farther from the previous border point than the preselected limit, and if so, the new border point is invalidated. It is then determined at step 285 if the present frame is between end diastolic and end systolic. If the frame is between end diastolic and end systolic, it is determined at step 286 if the previous border point is a threshold point and if the new border point is farther outward (away from the left ventricle centroid) from the previous border point by more than the preselected threshold border point movement limit. If so, the new border point is invalidated. If the same is true but the previous border point is not a threshold point, then at step 287 the new border point is invalidated. On the other hand, if the frame is between end systolic and end diastolic, it is determined at step 288 if the previous border point is a threshold point and if the new border point is closer to the left ventricle centroid than the previous border point by more than the preselected threshold border point movement limit. If so, the new border point is invalidated. If the same is true but the previous border point is not a threshold point, then at step 289 the new border point is invalidated. Upon exiting steps 287 or 289, or if the present frame is the ED frame, the process is repeated for the next ray of the selected type.

FIG. 2e illustrates in more detail a preferred embodiment of the algorithm for filling border gaps from the border of the previous frame as implemented in step 280. As shown, the process repeats at step 290 for all gaps in the detected border, and the processing path followed is based on whether the frames are determined at step 291 to be pre-edited or post-edited. If the frames are post-edit frames, all border points in the gap are replaced at step 292 with the Doppler-predicted border points for the present frame. In this case, the replacement of invalid border points in step 282 (FIG. 2c) is unnecessary. On the other hand, if the frames are pre-edit frames, at step 293 the two rays on either side of the gap in the present frame are used to compute the distances from the left ventricle centroid to the detected border points. This computation is then performed at step 294 for the two rays on either side of the gap in the previous frame. At step 295, the average difference in distance for these two rays is computed. Finally, at step 296, all border points in the gap with points that are the same distance from the left ventricle centroid as the border points on the corresponding rays of the previous frame (plus the average distance difference) are replaced. At step 282 (FIG. 2c), the invalid border points are then replaced with border points from the previous frame and corrected for translation of the LV centroid. If the gap cannot be filled in the pre-edit processing step, the gap is filled in the post-edit processing step by the Doppler-predicted boundary points.

Those skilled in the art will appreciate that the acquired boundary contours may be used to obtain both qualitative and quantitative information about the cardiac wall motion. To display the wall motion, the color quantization of the wall motion is displayed. Color quantization is desirable since it provides a visible aid for the physician to assess wall motion.

Figure 5:
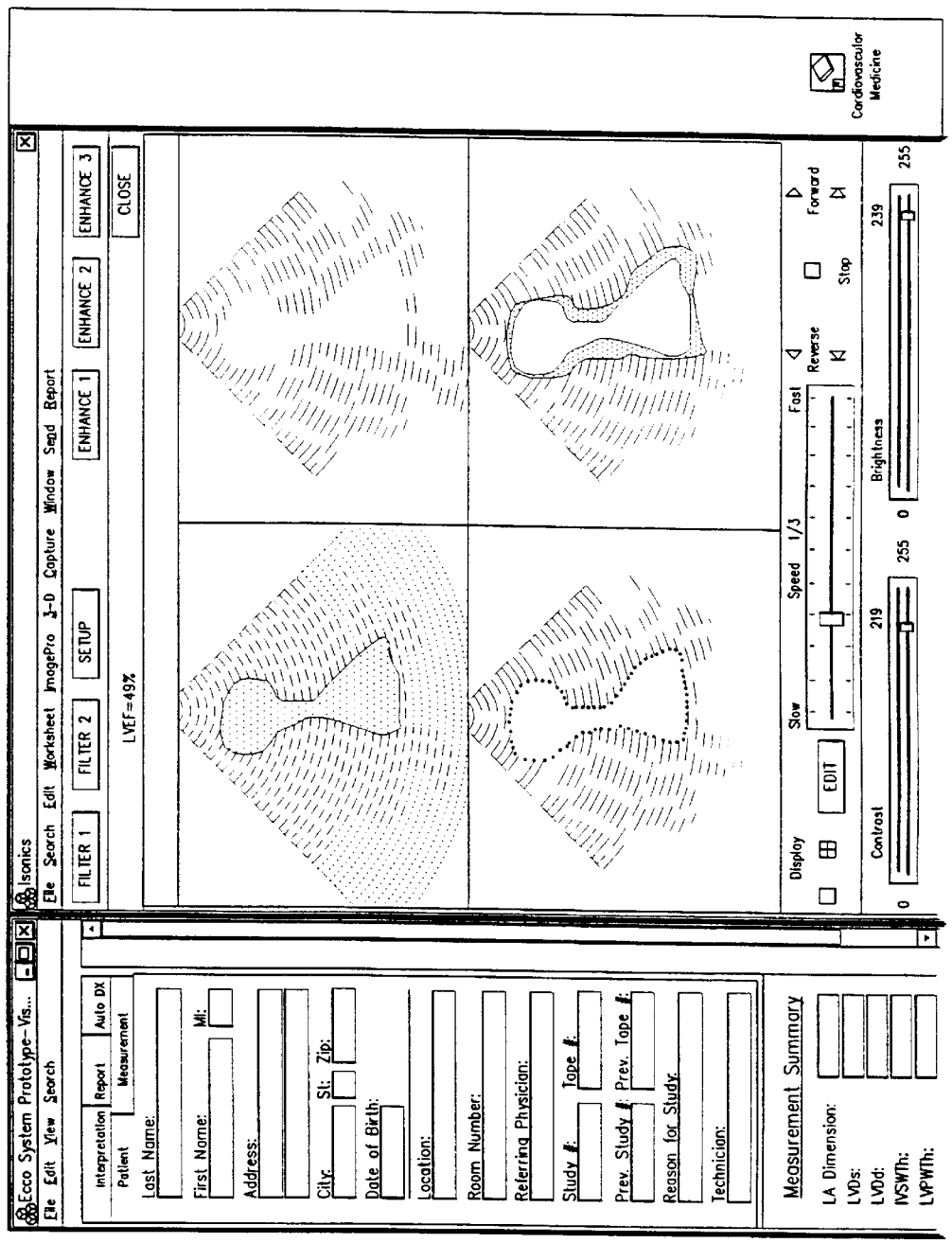
FIG. 5 illustrates a quad display of a captured echocardiogram raw data image, the speckle reduced image, the edge detected image, and the color quantitation of the movement of the image during the heart cycle along with a patient information screen.

In the preferred embodiment, using the above-described edge detection and left ventricular boundary location techniques, the endocardial wall on each video frame is outlined starting at end diastole and ending at end systole. To visualize the endocardial wall motion during the cardiac cycle, this information is displayed in accordance with the technique illustrated in FIG. 4. In particular, the interior portion of the left ventricle cavity corresponding to end diastole is filled with a single color (such as blue) at step 300. This blue area is then transferred to each frame of the sequence. Then, on each subsequent frame of the sequence, the left ventricle cavity on the current frame is filled with another color such as black at step 302. Thus, if the endocardial wall is contracting from frame to frame, the following effect is observed. Namely, on the end diastolic frame, the entire left ventricle cavity is black. On subsequent frames, the middle of the cavity is black, and an area corresponding to the motion of the endocardial wall is filled in with blue. This blue area thickens from frame to frame until end systole. As shown in FIG. 5 (lower right), such color quantization allows the viewer to easily visualize wall motion from end diastole to end systole and to ascertain the state of the contraction so that any asymmetry may be easily observed. In addition, this excursion of the wall may be quantitatively evaluated to help determine whether the wall motion is normal or abnormal and, if abnormal, what type of abnormality it is.

In particular, the wall motion may be quantitatively described at step 304 as follows. Assuming approximately 96 points are used for the edge detection (although more may be used if they are found to give better results), the ventricle may be divided into 6 main segments, beginning at north and at 60 degree increments moving clockwise. Each main segment is divided in half to yield 12 subsegments, with 8 samples per subsegment. The regional ejection fraction (Reg EF) for each subsegment is then calculated as:

Reg EF=Area end diastole−area end systole Area end diastole

Generally, a Regional EF greater than 50% is normal, while a Regional EF less than 50% is abnormal. Using the calculated regional area in each subsegment for the end diastolic and end systolic contours, respectively, these areas are modeled as a wedge shaped region. From this, the corresponding radial distance change of the end diastolic to end systolic regional contour (representing the average chord shortening in the subsegment) is calculated. The border is then colorized accordingly at step 306, thus providing easily readable wall motion analysis criteria.

In a preferred embodiment, the mean excursion of points of a particular segment is color coded at step 306 as follows:

>3.6 mm=NORMAL (green);

1.6–3.6 mm=HYPOKINETIC (yellow);

−0.5–1.5 mm=AKINETIC (red); and

<−0.5 mm=DYSKINETIC (blue).

Graphical user interface 26 may be used to assess myocardial perfusion using a spatial locator 22 and echocardiography images from video source 12 using the workstation 10. This capability is important, for the accurate localization of coronary artery disease and detection of small areas of reduced myocardial blood flow are important factors in clinical cardiac imaging. Further, the reliable localization of myocardial perfusion defects to one or more coronary arteries is of considerable practical importance.

Moreover, tomographic imaging of myocardial perfusion offers substantial promise for the accurate determination of the presence and extent of coronary artery disease by detecting smaller regions of ischemia (regions of insufficient blood flow) with improved capability for anatomic localization. Such factors have been validated with nuclear imaging techniques using thallium or sestamibi. Using a spatial locator 22, echocardiographic images are digitized by video digitizer 18 and stored in host memory 30 or 32. The images are acquired at "M" degree intervals with the 6 degrees of freedom coordinates stored with each image. After the injection of a contrast agent used for assessing perfusion by echocardiography (e.g., Albuminex) the images are acquired at the same "M" degree interval and 3-D coordinates as the images taken prior to the contrast injection. The contrast may be injected at peak exercise or pharmacologic stress. By using a tomographic display of the data, smaller areas of ischemia may be detected.

The quantitative measurements noted above may be used to assess myocardial perfusion and other parameters indicative of the heart's function. Generally, the user of the workstation 10 can view the echo directly from the echo machine (video source) 12, from digitized image sequences, or from videotape. Resting and stress studies may be displayed side-by-side so as to facilitate the detection of transient and sometimes subtle abnormalities in regional myocardial wall motion, wall thickening, and valvular function. During a conventional interpretation process, the physician accesses the menu items in a report generator program to evaluate normal and abnormal findings about the study. The data entries are recorded in the database 24 and then moved to a report form in the report generator.

While using the workstation 10 of the invention, a physician viewing a study may wish to process the digitized image sequences to improve their quality and diagnostic value. The physician may then choose one of several processing combinations from menus. The default is for processing average images with moderate speckle. However, the physician may also choose options for light or heavy speckle. After the speckle reduction, the physician may want to automatically outline the cardiac contour throughout the cardiac cycle. The physician selects this option which calls the border detection algorithm described above with respect to FIGS. 2a–2e. The physician can then select the color quantitation algorithm as described above with respect to FIG. 4 for a revealing view of the heart motion. A quad screen may be used to simultaneously show the raw image data, the speckle reduced image, the edge detected image, and the color quantitated image which illustrates movement of the endocardial walls (FIG. 5). Upon completion of the study, a report is typically generated (FIG. 10).

The report generator of the invention is preferably a routine which is called up to permit entry of patient data for storage in database 24. The patient information is entered via a patient information screen of the type shown in FIG. 5 and stored in the database 24 with a unique identifier for easy recall. Also, measurement data pertaining to the current study is entered via a measurement screen. The type of measurement is selected, e.g., 2-D, m-mode, Doppler, stress echo, or transesophogeal echo, and then the method and heart structure are selected. The measurement data is then entered and stored in database 24 in accordance with these selections. After the interpretation process by the physician, a report is generated for preview by the physician before the report is printed, e-mailed or faxed.

In accordance with an automatic interpretation feature of the invention ("AutoDx"), the measurements taken during the study are automatically compared to the database 24 to determine if any of the measurements are high or low. If any measurements are outside the expected range (abnormal), that area is color-coded to indicate the abnormal value which then triggers the selection of the corresponding abnormal finding which is automatically checked in an interpretation screen for that structure. The abnormal findings then are automatically listed in the findings summary section for inclusion in the report. However, during interpretation, the physician is given the opportunity to select the particular findings and to agree or disagree with the automatic analysis. If the physician agrees with the findings, the report is generated automatically and previewed before printing. On the other hand, if the physician disagrees with the findings, the physician may change or add to the findings in the interpretation section. The updated findings are then printed in the report.

Preferably, database 24 further includes a reference source "EchoHelp™" that the user can utilize to assist with the interpretation process. The reference source is a "what's this" type Help system for echocardiography that assists the physician with the interpretation by providing descriptions of abnormalities with lists of their known causes. When in the interpretation screen, the physician can highlight an abnormal finding in a selected structure, check its details, and call the EchoHelp™ feature to give a detailed differential diagnosis or explanation of the abnormality.

In a preferred embodiment of the invention, an expert system provides automatic interpretations of the echocardiograms. This expert system uses compiled lists of echo findings by disease, and diseases by echo findings. Questions about the findings may be addressed to the expert system. Also, the database 24 may be searched to match the findings to known diseases for the provision of a proposed diagnosis along with a text description of the disease and appropriate diagnosis criteria.

In accordance with the invention, the group of findings are compared to diagnostic data in the database 24 by the expert system for the determination of a suggested diagnosis. This suggested diagnosis and associated descriptive text is then displayed when an "AutoDx" or autodiagnosis option is selected by the physician at the time of interpretation. The "AutoDx" function compares the inputted findings to the findings of the expert system for generating a suggested diagnosis. When the "AutoDx" feature is selected during the interpretation process, the physician may select one or more of the suggested diagnoses for inclusion in the report.

For example, database 24 may contain findings for 150 or more cardiac diseases. After findings are entered, either manually or automatically, they are compared to the database 24, where each finding has its own number code of type 1, 2, or 3 as follows:

3=If patient has all of the 3's, then there is a high probability of diagnosis;

2=The patient must have all 2's or there cannot be a diagnosis;

1=Supporting findings; diagnosis is possible if patient has all 2's and more than half of the 1's.

Different values for data in the respective code types may be used to automatically identify diseases such as aortic stenosis, dilated cardiomyopathy, and aortic aneurysms.

A sample evaluation of an echocardiogram will now be described with respect to FIGS. 5–10.

In FIG. 5, the captured echocardiogram image is displayed in the display area. The technician is given the option of selecting "patient" to enter patient data, "measurement" to perform measurements, "interpretation" to interpret the displayed image, "AutoDx" to pull-up the suggested diagnosis of the expert system, and "report" to generate a report. As illustrated in FIG. 5, the technician may enter the patient data and make appropriate measurements for the respective structures by choosing the "patient" and "measurement" tabs, respectively. The study and the data entered by the technician is then stored for evaluation by the physician. During interpretation, the physician may select the "interpretation" tab to review the study and interpret the conditions of the various features of the heart by selecting the appropriate heart feature while evaluating the study. The physician may also select the "AutoDx" feature to assist with the interpretation process. Once the interpretation is complete, the physician may then select the "report" tab for generating a report.

Figure 6:
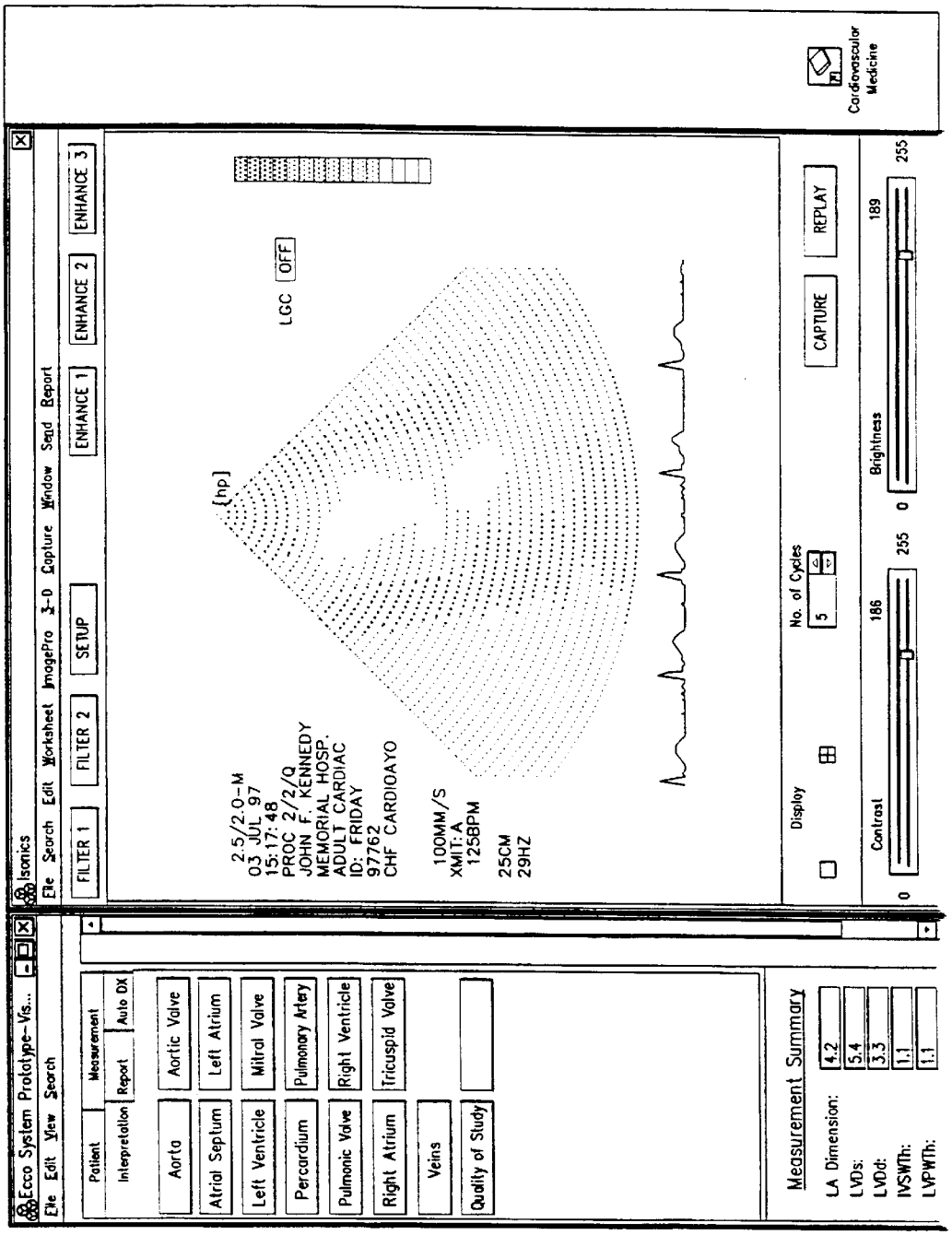
FIG. 6 illustrates an interpretation screen indicating the structures for selection for interpretation by the physician.
Figure 7:
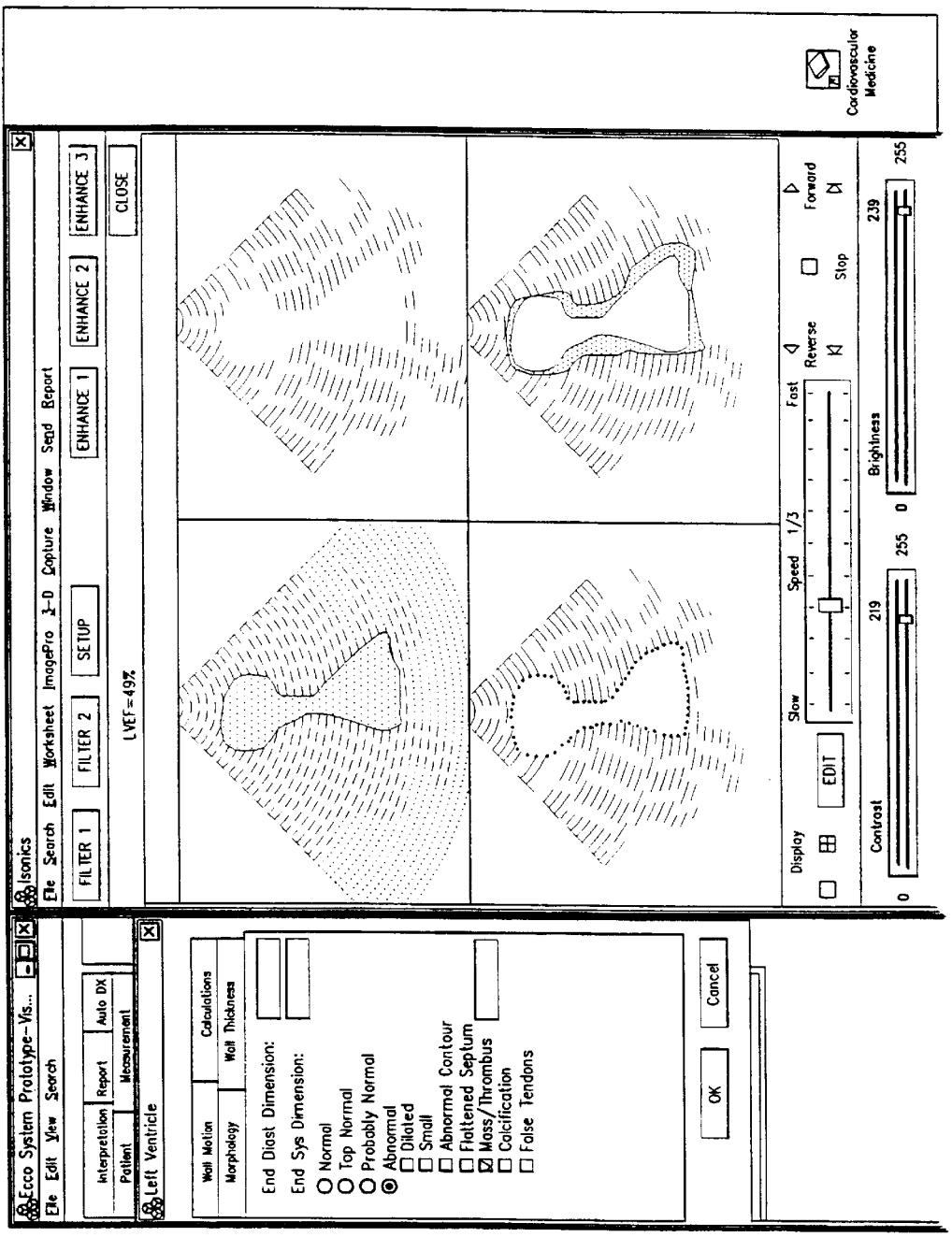
FIG. 7 illustrates a quad display of the raw image, the speckle reduced image, the edge detected image, and the color quantitation of the movement of the image during the heart cycle along with the abnormalities identified based on the measurement data.
Figure 8:
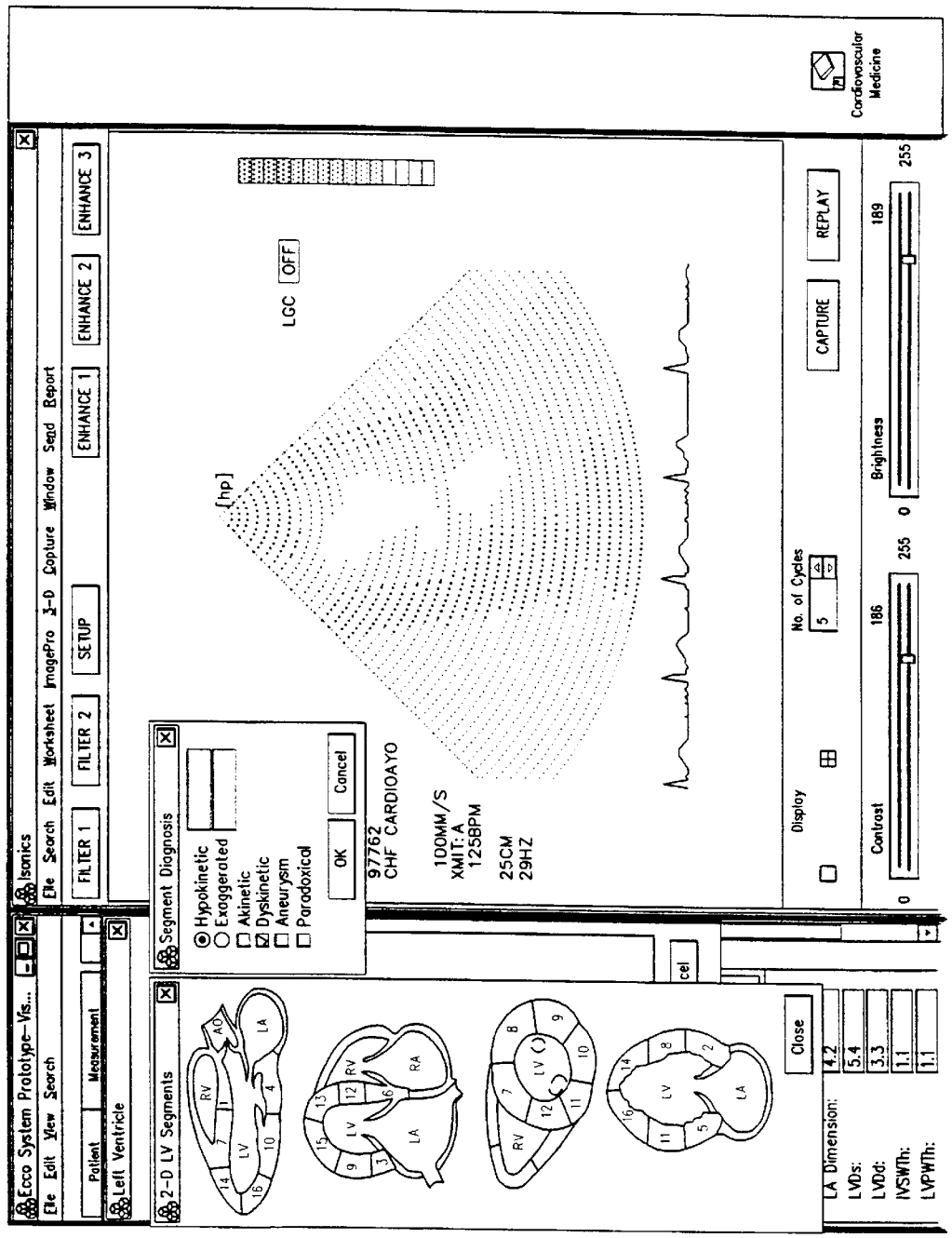
FIG. 8 illustrates the interpretation screen whereby the physician may enter a diagnosis of an echo-cardiogram for the selected heart segment.

In particular, during interpretation, the physician selects a structure to investigate from the screen of FIG. 6. For example, in FIG. 7, the physician has selected the left ventricle. FIG. 7 illustrates a quad presentation of the echocardiogram image of the left ventricle, where the upper left corner illustrates the raw echocardiogram, while the upper right corner illustrates the speckle reduced image. The lower left corner illustrates the edge detection determination, while the lower right corner illustrates the movement of the heart muscle during the heart cycle and is preferably color-coded. Any abnormalities determined by the expert system based on the measurement data entered by the technician also may be displayed. From this data, the physician can identify whether the left ventricle indeed appears to be normal or abnormal as indicated. If abnormal, the particular abnormality may be identified and selected. The physician may agree or disagree with the indication and enter his or her diagnosis via an interpretation screen of the type indicated in FIG. 8. The results are stored in the database 24 for inclusion in the report.

Figure 9:
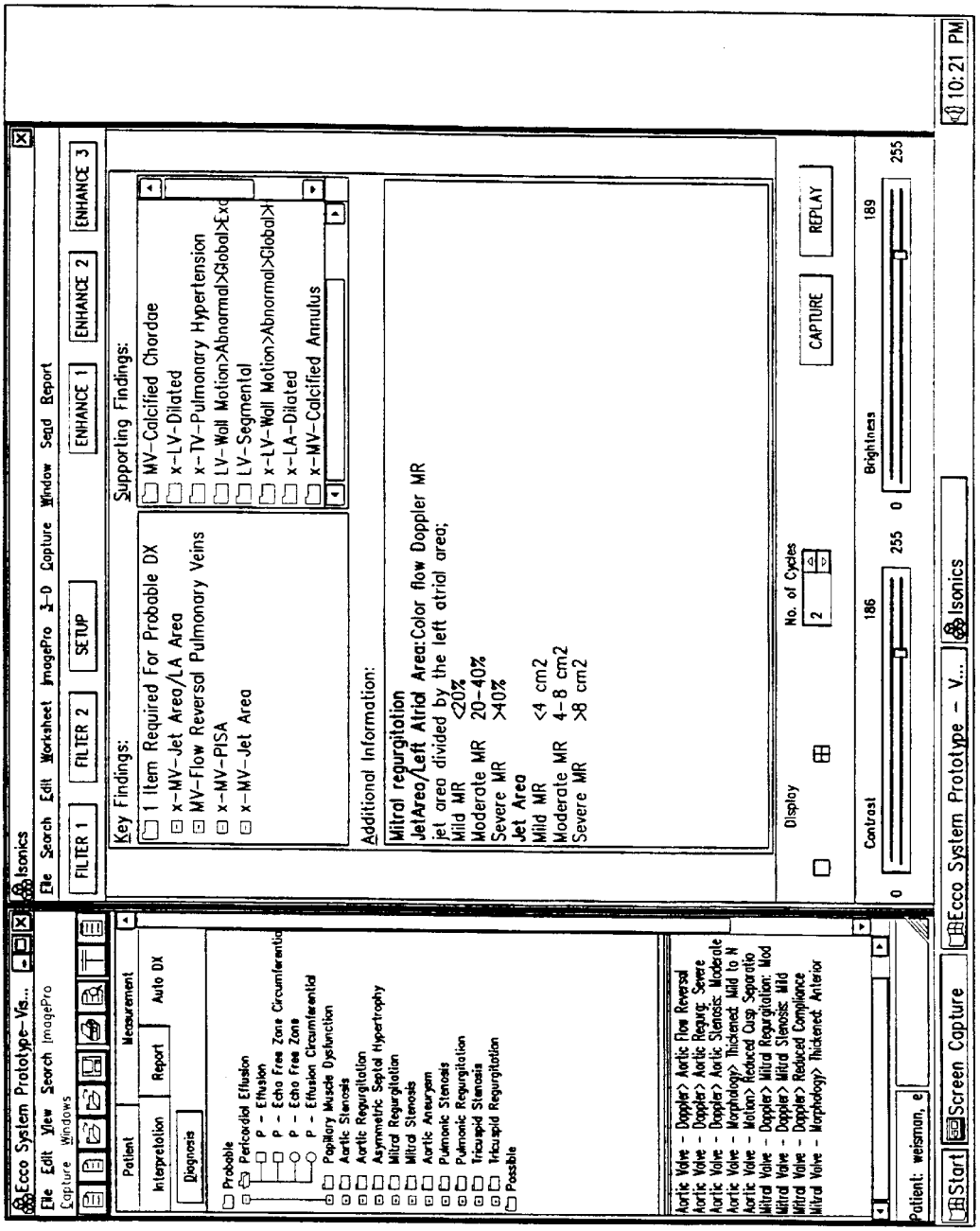
FIG. 9 illustrates a sample diagnosis "AutoDx" screen illustrating the possible diagnoses identified by the expert system.

FIG. 9 illustrates a sample segment diagnosis "AutoDx" screen. As described above, the group of abnormal findings is automatically compared to the database 24 by the expert system and a suggested diagnosis is returned. As illustrated, the suggested diagnoses are identified, and if selected, the corresponding diagnosis is automatically imported into the report generator.

Finally, when the interpretation is complete, the physician selects the report tab and previews the report stored in the database. The report lists all abnormal findings as they are chosen, either manually, or automatically, and illustrates what the physician has entered during the interpretation process for inclusion in the report. When the report is ready, it is printed, e-mailed, and/or faxed automatically. A sample echocardiography report generated by the report generator of the workstation 10 is illustrated in FIG. 10.

It will be appreciated by those skilled in the art that even though numerous characteristics and advantages of the present invention have been set forth in the foregoing description, together with details of the structure and function of the invention, the disclosure is illustrative only and numerous alternate embodiments are possible without departing from the novel teachings of the invention. Such modifications may be made in detail within the principles of the invention to the full extent indicated by the broad general meaning of the terms of the appended claims.

We claim:

1. An image processing system, comprising:
an image source which digitizes and outputs a video image of a patient's anatomy;
an image processor which implements at least one software process for processing a video image from said image source, said at least one software process removing noise from said video image while enhancing the definition of an internal structure of the patient's anatomy, automatically identifying a border of said internal structure and tracking movement of said border, and quantitating the extent of motion of at least said border of said internal structure of the patient's anatomy during a selected time frame; and
a display which displays a processed video image representative of the extent of motion of at least said border of said internal structure of the patient's anatomy during said selected time frame,
wherein said at least one software process removes noise from said video image while enhancing the definition of an internal structure of the patient's anatomy by performing a non-linear gray scale transformation on a received video image, recursively averaging the transformed video image, and performing a non-linear gray scale morphology operation on said transformed and averaged video image.

2. An image processing system as in claim 1, further comprising a spatial locator that registers position and orientation of a two-dimensional video image from said image source in a three-dimensional spatial coordinate system by overlaying a three-dimensional model of the patient's anatomy onto the two-dimensional video image at a corresponding position in three-dimensional space on said display.

3. An image processing system as in claim 1, further comprising a graphical user interface which permits a viewer to perform at least one of the following functions: view video images output by said image source, select alternative processing options, consult reference sources, generate reports from pull-down menus, and store, retrieve, and transmit said video images and reports including diagnostic interpretation of said video images by the viewer.

4. An image processing system as in claim 1, wherein said at least one software process implements said morphology operation by performing the steps of choosing a neighborhood of each pixel to be displayed, selecting rays of points in N directions in said neighborhood of said each pixel to be displayed, determining a minimum pixel value and a maximum pixel value along each ray of points and a minimum of the maximum pixel values for said rays of points (MIN of MAX) and a maximum of said minimum pixel values for said rays of points (MAX of MIN), and replacing said each pixel to be displayed with an average of said MIN of MAX and MAX of MIN values.

5. An image processing system, comprising:
an image source which digitizes and outputs a video image of a patient's heart, said image source including an image sequence synchronizer that synchronizes respective video image sequences of different frame lengths of the patient's heart;
an image processor which implements at least one software process for processing a video image from said image source, said at least one software process removing noise from said video image while enhancing the definition of a heart wall of the patient's heart, automatically identifying a border of said heart wall and tracking movement of said heart wall, and quantitating the extent of motion of at least said border of said heart wall of the patient's heart during a selected time frame; and
a display which displays a processed video image representative of the extent of motion of at least said border of said heart wall of the patient's heart during said selected time frame, wherein said image processor presents said respective synchronized video images of the patient's heart to said display for concurrent display, and
wherein said respective video image sequences of the patient's heart are synchronized by a synchronization process which computes target frame counts for systolic and diastolic portions of a cardiac cycle of the patient's heart, where the target systolic frames are $\sqrt{3.6N}$ and the target diastolic frames are N minus the target systolic frames, where N is the number of frames in a cardiac cycle of the patient's heart having a maximum number of frames in the cardiac cycle.

6. An image processing system as in claim 5, wherein said respective video image sequences of the patient's heart are synchronized and displayed in a synchronized M frame representation on said display whereby up to M viewing windows may be viewed concurrently.

7. An image processing system as in claim 5, wherein said synchronization process computes, for each cardiac cycle of each sequence of video images, a number of systolic frames to add as the target systolic frame minus $\sqrt{3.6N}$ (ADD SYS FRAMES), and a number of diastolic frames to add as the target diastolic frame minus $(N-\sqrt{3.6N})$ (ADD DIA FRAMES), where N is the number of frames in the cardiac cycle.

8. An image processing system as in claim 7, wherein said synchronization process repeats the systolic frames from frame $\sqrt{3.6N}$ to frame $\sqrt{3.6N}$ minus ADD SYS FRAMES, repeats the diastolic frames for all frames in a range $\sqrt{3.6N}+1$ to N by $\text{int}(\text{ADD DIA FRAMES}/\sqrt{3.6N})$ times, and repeats all frames in a range $M=\sqrt{3.6N}+[N-\sqrt{3.6N}-\text{MOD}(\text{ADD DIA FRAMES})* \sqrt{3.6N}]/2$ to $M+\text{MOD}(\text{ADD DIA FRAMES}, \sqrt{3.6N})$ one time each, whereby each sequence of images of a cardiac cycle has the same number of image frames.

9. An image processing system, comprising:
- an image source which digitizes and outputs a video image of a patient's heart;
- an image processor which implements at least one software process for processing a video image from said image source, said at least one software process removing noise from said video image while enhancing the definition of a heart wall of the patient's heart, automatically identifying a border of said heart wall and tracking movement of said heart wall, and quantitating the extent of motion of at least said border of said heart wall of the patient's heart during a selected time frame; and
- a display which displays a processed video image representative of the extent of motion of at least said border of said heart wall of the patient's heart during said selected time frame,
- wherein said at least one software process automatically identifies a border of said heart wall and tracks movement of said border by tagging frames of said video image of the patient's heart corresponding to end-diastole (ED frame) and end-systole (ES frame) of a selected cardiac cycle, tracing said border of said heart wall, computing thresholds from the ED frame, and detecting borders of said heart wall for all frames of said selected cardiac cycle using said thresholds.

10. An image processing system as in claim 9, wherein said at least one software process further comprises an expert system that evaluates data from said video image of the patient's heart and suggests to a viewer various diagnostic possibilities that are consistent with the video image of the patient's heart.

11. An image processing system as in claim 9, wherein said at least one software process further comprises a report generator which accepts diagnostic data from a viewer and generates a diagnostic report including at least said diagnostic data.

12. An image processing system as in claim 9, wherein said at least one software process further comprises a help system which is accessed by a viewer during interpretation of the video image of the patient's heart to provide descriptions of abnormalities of the heart structure with lists of known causes of said abnormalities.

13. An image processing system as in claim 9, wherein said at least one software process computes thresholds from the ED frame by setting a preset threshold, projecting N rays spaced at approximately equal angles from a centroid of the traced heart wall border, determining image gray-level gradient points along each of said N rays in a vicinity of said traced heart wall border, and, if a gradient point larger than said preset threshold is found along one of said N rays, replacing a border point on said traced heart wall border with said gradient point.

14. An image processing system as in claim 13, wherein said at least one software process further determines, for each of M threshold values from 0 to a maximum gray level, a histogram equalized threshold value, thresholds said ED frame using the histogram equalized threshold value, performs morphological opening and closing of said ED frame, finds, starting on the traced heart wall border for said ED frame, a change state point on each ray where the thresholded ED image changes state, and, for each ray, determines an error distance between the change state point and the traced heart wall border.

15. An image processing system as in claim 14, wherein said at least one software process further divides a portion of said ED frame representing a left ventricle of the patient's heart into N pie-shaped segments, identifies a selected threshold for each segment that corresponds to a smallest average error distance for that segment, compares the video image to the selected threshold, computes an average error distance for each segment using the selected threshold, and, for each segment, saves the selected threshold value as representative of said border of the patient's heart wall if all points of the selected threshold are outside of an existing heart wall border or if the average error distance is less than a previous average error distance multiplied by a predetermined weighting factor.

16. An image processing system as in claim 15, wherein said at least one software process compares an image in each frame of said video signal in said selected cardiac cycle to selected threshold values for each segment, performs morphological opening and closing of each image, and invalidates border points which are beyond said selected threshold values for the segment containing said border points.

17. An image processing system as in claim 16, wherein said at least one software process finds image gray-level gradient points along each ray in the vicinity of the border of the previous frame of said video signal for invalidated border points and invalidates the gradient points if a border point on a corresponding ray of the previous frame of said video signal was also determined from image gray-level gradient points.

18. An image processing system as in claim 16, wherein said at least one software process fills in gaps less than a predetermined number of rays in said traced border of the heart wall by interpolating border points on said traced border of the heart wall on either side of the gaps.

19. An image processing system as in claim 18, wherein said at least one software process fills in gaps greater than said predetermined number of rays in said traced border of the heart wall by replacing border points in said gaps with Doppler-predicted border points for a present frame of said video signal.

20. An image processing system as in claim 18, wherein said at least one software process fills in gaps greater than said predetermined number of rays in said traced border of the heart wall by computing for two rays on either side of a gap distances from the centroid of the traced heart wall border to the border points on either side of said gap for a present frame and a previous frame of said video signal, computing an average distance of said distances for said present frame and said previous frame, and replacing all border points in said gap with points that are the same distance from the centroid of the traced heart wall border as the border points on corresponding rays of the previous frame plus the computed average distance difference.

21. An image processing system as in claim 20, wherein said at least one software process replaces invalid border points in said traced border of the heart wall with border points from said previous frame of said video signal after correction for translation of the centroid of the traced heart wall border from said previous frame to the present frame of said video signal.

22. An image processing system as in claim 21, wherein said at least one software process translates the centroid of the traced heart wall border from said previous frame to the present frame of said video signal by tracing the heart wall border for said previous frame and said present frame of said video signal, dividing the traced heart wall border from said previous frame into a first predetermined number of border points equally spaced with respect to arc length along said traced heart wall border, dividing the traced heart wall border of said present frame into a second predetermined number of border points equally spaced with respect to arc length along said traced wall border, finding, for each point on the traced heart wall border of the previous frame, a replacement point on the traced heart wall border of the present frame which is nearest to a point on the traced heart wall border of the previous frame, and replacing a corresponding border point of the previous frame with the replacement point.

23. An image processing system, comprising:

an image source which digitizes and outputs a video image of a patient's heart;

an image processor which implements at least one software process for processing a video image from said image source, said at least one software process removing noise from said video image while enhancing the definition of a heart wall of the patient's heart, automatically identifying a border of said heart wall and tracking movement of said heart wall, and quantitating the extent of motion of at least said border of said heart wall of the patient's heart during a selected time frame; and a display which displays a processed video image representative of the extent of motion of at least said border of said heart wall of the patient's heart during said selected time frame, wherein said at least one software process quantitates the extent of motion of at least said border of said heart wall from end-diastole to end-systole by representing frame to frame movement of said heart wall in a color which is different from a background color of the processing video image displayed on said display.

24. An image processing system as in claim 23, wherein said at least one software process color codes the extent of radial movement of radial sections of said heart wall from end-diastole to end-systole.

25. A method of imaging internal anatomy of a patient, comprising the steps of:

capturing a video image of the patient's internal anatomy;

removing noise from said video image while enhancing the definition of an internal structure of the patient's anatomy;

automatically identifying a border of said internal structure;

tracking movement of said border;

quantitating the extent of motion of at least said border of said internal structure of the patient's anatomy during a selected time frame; and displaying processed video images representative of the extent of motion of at least said border of said internal structure of the patient's anatomy during said selected time frame, wherein said noise removing step comprises the steps of performing a non-linear gray scale transformation on a captured video image, recursively averaging the transformed video image, and performing a non-linear gray scale morphology operation on said transformed and averaged video image.

26. A method as in claim 25, further comprising the step of registering a position and orientation of two-dimensional captured video images in a three-dimensional spatial coordinate system by overlaying a three-dimensional model of the patient's anatomy onto the two-dimensional video image at a corresponding position in three-dimensional space for display in three dimensions.

27. A method as in claim 26, further comprising the step of calculating a 3-D volume of the patient's anatomy from said two-dimensional captured video images and said three-dimensional model of the patient's anatomy.

28. A method as in claim 26, further comprising the steps of injecting a contrast agent into the patient's bloodstream after capturing the video image of the patient's internal anatomy at M degree intervals, capturing a video image of the patient's internal anatomy at said M degree intervals at points of injection of said contrast agent, and tomographically displaying said video images before and after injection of said contrast agent.

29. A method as in claim 25, wherein morphology operation comprises the steps of choosing a neighborhood of each pixel to be displayed, selecting rays of points in N directions in said neighborhood of said each pixel to be displayed, determining a minimum pixel value and a maximum pixel value along each ray of points and a minimum of the maximum pixel values for said rays of points (MIN of MAX) and a maximum of said minimum pixel values for said rays of points (MAX of MIN), and replacing said each pixel to be displayed with an average of said MIN of MAX and MAX of MIN values.

30. A method of imaging internal anatomy of a patient, comprising the steps of:

capturing a video image of the patient's internal anatomy;

removing noise from said video image while enhancing the definition of an internal structure of the patient's anatomy;

automatically identifying a border of said internal structure;

tracking movement of said border;

quantitating the extent of motion of at least said border of said internal structure of the patient's anatomy during a selected time frame; and displaying processed video images representative of the extent of motion of at least said border of said internal structure of the patient's anatomy during said selected time frame, wherein said video image is a video image of a patient's heart and said step of automatically identifying a border of said internal structure comprises the steps of tagging frames of said video image of the patient's heart corresponding to end-diastole (ED frame) and end-systole (ES frame) of a selected cardiac cycle, tracing said border of said heart wall, computing thresholds from the ED frame, and detecting borders of said heart wall for all frames of said selected cardiac cycle using said thresholds.

31. A method as in claim 30, wherein said step of automatically identifying a border of said internal structure comprises the steps of computing thresholds from the ED frame by setting a preset threshold, projecting N rays spaced at approximately equal angles from a centroid of the traced heart wall border, determining image gray-level gradient points along each of said N rays in a vicinity of said traced heart wall border, and, if a gradient point larger than said preset threshold is found along one of said N rays, replacing a border point on said traced heart wall border with said gradient point.

32. A method as in claim 31, comprising the further step of determining, for each of M threshold values from 0 to a maximum gray level, a histogram equalized threshold value, thresholding said ED frame using the histogram equalized threshold value, performing morphological opening and closing of said ED frame, finding, starting on the traced heart wall border for said ED frame, a change state point on each ray where the thresholded ED image changes state, and, for each ray, determining an error distance between the change state point and the traced heart wall border.

33. A method as in claim 32, comprising the further steps of dividing a portion of said ED frame representing a left ventricle of the patient's heart into N pie-shaped segments, identifying a selected threshold for each segment that corresponds to a smallest average error distance for that segment, comparing the video image to the selected threshold, computing an average error distance for each segment using the selected threshold, and, for each segment, saving the selected threshold value as representative of said border of the patient's heart wall if all points of the selected threshold are outside of an existing heart wall border or if the average error distance is less than a previous average error distance multiplied by a predetermined weighting factor.

34. A method as in claim 33, comprising the further steps of comparing an image in each frame of said video signal in said selected cardiac cycle to selected threshold values for each segment, performing morphological opening and closing of each image, and invalidating border points which are beyond said selected threshold values for the segment containing said border points.

35. A method as in claim 34, comprising the further steps of finding image gray-level gradient points along each ray in the vicinity of the border of the previous frame of said video signal for invalidated border points and invalidating the gradient points if a border point on a corresponding ray of the previous frame of said video signal was also determined from image gray-level gradient points.

36. A method as in claim 34, comprising the additional step of filling in gaps less than a predetermined number of rays in said traced border of the heart wall by interpolating border points on said traced border of the heart wall on either side of the gaps.

37. A method as in claim 36, comprising the additional step of filling in gaps greater than said predetermined number of rays in said traced border of the heart wall by replacing border points in said gaps with Doppler-predicted border points for a present frame of said video signal.

38. A method as in claim 36, comprising the additional step of filling in gaps greater than said predetermined number of rays in said traced border of the heart wall by computing for two rays on either side of a gap distances from the centroid of the traced heart wall border to the border points on either side of said gap for a present frame and a previous frame of said video signal, computing an average distance of said distances for said present frame and said previous frame, and replacing all border points in said gap with points that are the same distance from the centroid of the traced heart wall border as the border points on corresponding rays of the previous frame plus the computed average distance difference.

39. A method as in claim 38, wherein said step of replacing invalid border points comprises the step of replacing invalid border points in said traced border of the heart wall with border points from said previous frame of said video signal after correcting for translation of the centroid of the traced heart wall border from said previous frame to the present frame of said video signal.

40. A method in claim 39, wherein said step of translating the centroid of the traced heart wall border from said previous frame to the present frame of said video signal comprises the steps of tracing the heart wall border for said previous frame and said present frame of said video signal, dividing the traced heart wall border from said previous frame into a first predetermined number of border points equally spaced with respect to arc length along said traced heart wall border, dividing the traced heart wall border of said present frame into a second predetermined number of border points equally spaced with respect to arc length along said traced wall border, finding, for each point on the traced heart wall border of the previous frame, a replacement point on the traced heart wall border of the present frame which is nearest to a point on the traced heart wall border of the previous frame, and replacing a corresponding border point of the previous frame with the replacement point.

41. A method of imaging internal anatomy of a patient, comprising the steps of:

capturing a video image of the patient's internal anatomy;

removing noise from said video image while enhancing the definition of an internal structure of the patient's anatomy;

automatically identifying a border of said internal structure;

tracking movement of said border;

quantitating the extent of motion of at least said border of said internal structure of the patient's anatomy during a selected time frame; and displaying processed video images representative of the extent of motion of at least said border of said internal structure of the patient's anatomy during said selected time frame, wherein said video image is a video image of a patient's heart, and said step of quantitating the extent of motion of at least said border of said heart wall from end-diastole to end-systole during said selected time frame comprising the step of quantitating the extent of motion of at least said border by representing frame to frame movement of said heart wall in a color which is different from a background color of the processing video image displayed on said display.

42. A method as in claim 41, wherein said quantitating step comprises the additional step of color coding the extent of radial movement of radial sections of said heart wall from end-diastole to end-systole.

43. A method of imaging a patient's heart, comprising the steps of:

capturing respective video images of a patient's heart;

removing noise from said video images while enhancing the definition of an internal structure of the patient's heart;

automatically identifying a border of said heart;

tracking movement of said border;

quantitating the extent of motion of at least said border of said heart during a selected time frame;

synchronizing said respective video images of the patient's heart; and displaying said synchronized images in a synchronized M frame representation whereby up to M viewing windows may be viewed concurrently, wherein said synchronization step comprises the step of computing target frame counts for systolic and diastolic portions of a cardiac cycle of the patient's heart, where the target systolic frames are $\sqrt{3.6N}$ and the target diastolic frames are N minus the target systolic frames, where N is the number of frames in a cardiac cycle of the patient's heart having a maximum number of frames in the cardiac cycle.

44. A method in claim 43, wherein said synchronization step comprises the additional step of computing, for each cardiac cycle of each sequence of video images, a number of systolic frames to add as the target systolic frame minus $\sqrt{3.6N}$ (ADD SYS FRAMES), and a number of diastolic frames to add as the target diastolic frame minus $(N-\sqrt{3.6N})$ (ADD DIA FRAMES), where N is the number of frames in the cardiac cycle.

45. A method as in claim 44, wherein said synchronization step comprises the steps of repeating the systolic frames from frame $\sqrt{3.6N}$ to frame $\sqrt{3.6N}$ minus ADD SYS FRAMES, repeating the diastolic frames for all frames in a range $\sqrt{3.6N}+1$ to N by $\text{int}(\text{ADD DIA FRAMES}/\sqrt{3.6N})$ times, and repeating all frames in a range $M=\sqrt{3.6N}+[N-\sqrt{3.6N}-\text{MOD}(\text{ADD DIA FRAMES})*\sqrt{3.6N}]/2$ to $M+\text{MOD}(\text{ADD DIA FRAMES}, \sqrt{3.6N})$ one time each, whereby each sequence of images of a cardiac cycle has the same number of image frames.

46. A method as in claim 43, comprises the additional steps of accepting diagnostic data from a viewer and generating a diagnostic report including at least said diagnostic data.

\* \* \* \* \*

UNITED STATES PATENT AND TRADEMARK OFFICE
CERTIFICATE OF CORRECTION

PATENT NO. : 6,674,879 B1
DATED : January 6, 2004
INVENTOR(S) : Weisman et al.

It is certified that error appears in the above-identified patent and that said Letters Patent is hereby corrected as shown below:

<u>Column 7,</u>
Line 10, delete ""IN"" and insert therefor -- "N" --.

<u>Column 12,</u>
Line 5, delete "Reg EF=Area end diastole end systole Area end diastole" and insert therefor, the following:
-- <u>Reg EF = Area end diastole - area end systole</u>
 Area end diastole --.

Signed and Sealed this

Thirteenth Day of April, 2004

JON W. DUDAS
*Acting Director of the United States Patent and Trademark Office*